(12) United States Patent
Scialò et al.

(10) Patent No.: US 12,399,089 B2
(45) Date of Patent: Aug. 26, 2025

(54) LIQUID IMPINGER SAMPLING SYSTEMS AND METHODS

(71) Applicant: PARTICLE MEASURING SYSTEMS, INC., Boulder, CO (US)

(72) Inventors: Giovanni Scialò, Frascati (IT); Davide Recchia, Frascati (IT)

(73) Assignee: PARTICLE MEASURING SYSTEMS, INC., Boulder, CO (US)

( * ) Notice: Subject to any disclaimer, the term of this patent is extended or adjusted under 35 U.S.C. 154(b) by 608 days.

(21) Appl. No.: 17/848,751

(22) Filed: Jun. 24, 2022

(65) Prior Publication Data

US 2023/0009668 A1 Jan. 12, 2023

Related U.S. Application Data

(60) Provisional application No. 63/220,176, filed on Jul. 9, 2021.

(51) Int. Cl.
*G01N 33/497* (2006.01)
*G01N 1/22* (2006.01)

(52) U.S. Cl.
CPC .......... *G01N 1/2247* (2013.01); *G01N 33/497* (2013.01); *G01N 2001/227* (2013.01)

(58) Field of Classification Search
CPC .............. G01N 1/2247; G01N 33/497; G01N 2001/227
See application file for complete search history.

(56) References Cited

U.S. PATENT DOCUMENTS 1,526,170 A 2/1925 Milligan
1,541,853 A 6/1925 Rottmann
(Continued)

FOREIGN PATENT DOCUMENTS

BR PI0904216 A2 6/2011
CN 104211699 A 12/2014
(Continued)

OTHER PUBLICATIONS

Anwar et al. (2010) "Virus collection efficiency of biosampler versus impinger with variable time and flow rate," Senior Thesis, University of Florida: Department of Chemical Engineering and Environmental Engineering and Sciences.
(Continued)

*Primary Examiner* — Guy K Townsend
(74) *Attorney, Agent, or Firm* — LEYDIG VOIT & MAYER, LTD.

(57) ABSTRACT

Disclosed is a liquid impinger, for example a liquid impinger, particularly a disposable liquid impinger. The liquid impinger comprises, for example, at least one nozzle positioned in the interior and attached to the bottom portion. In some aspects, the liquid impinger comprises a polymeric material. Also disclosed are methods of making the liquid impinger comprising, for example, forming at least two components, assembling the at least two components into the liquid impinger, filling the liquid impinger with liquid, and exposing the filled liquid impinger to radiation for sterilization prior to use. Also disclosed are methods of using the liquid impinger, for example, by transporting a gas comprising analytes through the liquid impinger and transferring at least a portion of the analytes from the gas into the liquid contained therein. The method further comprises, for example, after transferring analytes form the gas into the liquid, incubating and/or detecting at least a portion of the analytes in the liquid without removing the liquid from the liquid impinger.

20 Claims, 15 Drawing Sheets

(56) References Cited

U.S. PATENT DOCUMENTS

| | | | |
|---|---|---|---|
| 3,495,440 | A | 2/1970 | Koblin et al. |
| 4,162,971 | A | 7/1979 | Zlokarnik et al. |
| 4,363,639 | A | 12/1982 | Gladon |
| 5,902,385 | A | 5/1999 | Willeke et al. |
| 5,904,752 | A | 5/1999 | Willeke |
| 6,520,034 | B1 | 2/2003 | Masquelier et al. |
| 6,550,347 | B2 | 4/2003 | Bradley |
| 6,605,446 | B2 | 8/2003 | Eden |
| 7,208,123 | B2 * | 4/2007 | Knollenberg ........ G01N 29/022 422/50 |
| 7,699,915 | B2 | 4/2010 | Lin |
| 7,985,949 | B2 * | 7/2011 | Rodier ................. G01N 27/622 250/281 |
| 8,054,082 | B2 * | 11/2011 | Brothier ............. G01N 33/0047 250/389 |
| 9,638,665 | B2 * | 5/2017 | Gorbunov .......... G01N 15/0266 |
| 9,885,640 | B2 | 2/2018 | Ketcham et al. |
| 10,345,200 | B2 * | 7/2019 | Scialo ................. G01N 1/2208 |
| 10,371,620 | B2 * | 8/2019 | Knollenberg ...... G01N 15/1425 |
| 10,392,385 | B2 | 8/2019 | Kamal et al. |
| 10,859,487 | B2 * | 12/2020 | Knollenberg ........... G01F 1/704 |
| 11,231,345 | B2 * | 1/2022 | Scialo ................. C12N 5/0665 |
| 11,255,760 | B2 * | 2/2022 | Scialo ................. G01N 15/0205 |
| 11,268,930 | B2 * | 3/2022 | Rodier ............... G01N 15/1459 |
| 11,892,462 | B2 * | 2/2024 | Scialò ................ G01N 15/1433 |
| 11,927,509 | B2 * | 3/2024 | Scialo ................ G01N 35/0099 |
| 2004/0152150 | A1 | 8/2004 | Eden |
| 2005/0136507 | A1 | 6/2005 | Sullivan et al. |
| 2008/0028832 | A1 | 2/2008 | Sullivan et al. |
| 2008/0142424 | A1 | 6/2008 | Kitasko et al. |
| 2009/0078862 | A1 * | 3/2009 | Rodier ................ G01N 27/622 250/288 |
| 2015/0018384 | A1 | 1/2015 | Lin et al. |
| 2015/0082864 | A1 * | 3/2015 | Chen .................... G01N 1/2202 73/19.12 |
| 2016/0320359 | A1 * | 11/2016 | Chuang .................... G01N 1/10 |
| 2020/0072729 | A1 * | 3/2020 | Lumpkin ........... G01N 15/1459 |
| 2020/0158603 | A1 * | 5/2020 | Scialo ................. G01N 1/2202 |
| 2020/0269198 | A1 * | 8/2020 | Stevenson ........ B01F 23/23123 |
| 2021/0063349 | A1 * | 3/2021 | Rodier ................. G01N 27/622 |
| 2021/0223273 | A1 * | 7/2021 | Scialò .................. G01N 1/2273 |
| 2023/0009668 | A1 * | 1/2023 | Scialò .................. G01N 33/497 |

FOREIGN PATENT DOCUMENTS

| | | |
|---|---|---|
| CN | 104628722 B | 6/2016 |
| CN | 106432235 A | 2/2017 |
| CN | 105037350 B | 9/2017 |
| CN | 105294826 B | 9/2018 |
| CN | 109575020 A | 4/2019 |
| CN | 111303148 A | 6/2020 |
| CN | 111943948 A | 11/2020 |
| GB | 458583 A | 12/1936 |
| JP | S483192 U | 1/1973 |
| JP | 2000035385 A | 2/2000 |
| WO | WO 1982/03713 A1 | 10/1982 |
| WO | WO 1991/015287 A1 | 10/1991 |
| WO | WO 2015/186090 | 12/2015 |

OTHER PUBLICATIONS

Ghasemi et al. (2014) "3D-QSAR and Docking Studies of a Series of β-Carboline Derivatives as Antitumor Agents of PLK1," Journal of Chemistry, vol. 2014, Article ID 323149, 10 pp. https://doi.org/10.1155/2014/323149.

Kesavan et al. (2010) "Sampling and Retention Efficiencies of Batch-Type Liquid-Based Bioaerosol Samplers," Aerosol Science and Technology, 44:10, 817-829, DOI: 10.1080/02786826.2010.497513.

Li et al. (2015) "Synthesis and Fungicidal Activity of β-Carboline Alkaloids and Their Derivatives," Molecules, 20, 13941-13957. doi: 10.3390/molecules200813941.

Panice et al. (2019) "New 3-tetrazolyl-β-carbolines and β-carboline-3-carboxylates with anti-cancer activity," European Journal of Medicinal Chemistry, 179, 123-132.

European Search Report and Written Opinion issued in EP 22 838 242.0 on Feb. 19, 2025.

Int'l Search Report and Written Opinion issued in PCT/US2022/034871 mailed on Nov. 22, 2022.

Wang et al. (Aug. 2024) "Effect of back-pressure on absorption efficiency of impingers used for air sampling" Water Science and Technology 50(4): 125-130 doi.org/10.2166/wst.2004.0240.

* cited by examiner

LIQUID IMPINGER SAMPLING SYSTEMS AND METHODS

CROSS-REFERENCE TO RELATED APPLICATIONS

This application claims the benefit of priority to U.S. Provisional Patent Application No. 63/220,176, filed Jul. 9, 2021, which is hereby incorporated by reference in its entirety.

BACKGROUND

This invention is generally in the field of particle sampling, collection and analysis. The invention generally relates to devices and methods for sampling and characterizing particles in gases including air and process chemicals for applications including the evaluation of viable biological contaminants in a range of cleanroom and manufacturing environments.

Monitoring gas streams for the presence of contaminants, including viable biological particles, is of importance in a number of industries, including pharmaceuticals and biologicals, food and beverages, and cosmetics. The presence of particles even at very low levels in these industries may detrimentally impact manufacturing processes and product integrity or quality. Moreover, regulatory conditions and industry standards include establishing and maintaining low particle levels to comply with the requirements of relevant process condition certifications. For example, in the manufacture of pharmaceutical and biologicals, contamination by airborne particulates consisting of viable biological contaminants puts therapeutic products at risk due to health and safety concerns requiring compliance with stringent standards established by the US Food and Drug Administration (FDA) and other foreign and international health regulatory agencies.

To address the impact of particulate contamination, cleanrooms and clean zones are commonly employed in diverse manufacturing and fabrication settings and facilities wherein the presence and amounts of particles and other contaminants are actively monitored and documented. Standards for the classification of cleanroom particle levels and standards for testing and monitoring to ensure compliance are provided by ISO 14664-1 and 14664-2. Aerosol optical particle counters are commonly used to determine the airborne particle contamination levels in cleanrooms and clean zones, and liquid particle counters are used to optically measure particle contamination levels in process gases. Where microbiological particles are a particular concern, such as in the pharmaceuticals and biologicals industries, not only is quantification of the number of airborne particles important, but characterizing the viability and identity of microbiological particles is also at issue. ISO 14698-1 and 14698-2 provide standards for evaluation of cleanroom and clean zone environments for biocontaminants.

Various liquid impingers and methods are known for collection, analysis and monitoring for the presence of viable biological particles in a gas stream for cleanroom applications, including settling plates, contact plates, surface swabbing, fingertip sampling, agar-filled petri dishes, impactor-based samplers and liquid impingers. For these types of biological particle collection and analysis techniques, various operational aspects are important to ensure efficient collection, detection and analysis. For example, the collection efficiency may be of high importance, as failing to detect that biological particles are present in cleanroom air can result in the cleanroom environment having higher levels of contamination than detected. Upon determination that under counting has occurred, pharmaceutical products made in those environments can be identified as failing to meet required standards, potentially leading to costly product recalls. Similarly, failing to ensure that the viability of collected biological particles is maintained during the collection process will also result in under counting. Such a situation can arise, for example, if the collected biological particles are destroyed, damaged or otherwise rendered non-viable upon collection and growth, such that the collected particles do not replicate during the incubation process and, therefore, cannot be subsequently identified.

On the opposite extreme, biological particle concentrations can be overestimated due to the occurrence of false positives. Over counting of this nature arises where a biological particle that is not collected from the cleanroom air, but is otherwise placed in contact with the growth medium, is allowed to replicate during the incubation process and is improperly identified as originating from the cleanroom air. Situations that contribute to false positives include failing to properly sterilize the collection medium and collection system prior to particle collection and improper handling of the growth medium by cleanroom personnel as it is installed into a particle collection system and/or removed from the particle collection system and placed into the incubator. Again, this can result in a pharmaceutical product being identified as failing to meet required standards. Without sufficient measures to identify false positives, such a situation can result in pharmaceutical products that actually meet the required standards, but are destroyed due to an overestimation of biological particle concentration in the cleanroom air indicating that the standards were not met.

Some solutions, such as single-use agar-filled petri dishes and single use impactors, permit noncontact of the media through the growing/incubation step, but detection or recognition are often manually performed, with possible contamination from human manipulation/intervention, which may result in the occurrence of false positives. Single use impactor-based samplers, such as those described in U.S. Pat. No. 10,345,200, for example, provides single use, impactor-based air samplers designed to allow sterilization, sampling collection and/or readout in a fully integrated configuration resulting in lower susceptibility of false positives. The time required to incubate or grow the microorganisms sampled in the agar petri dishes and single use, impactors, however, is typically several days, which can cause an undesired delay between sampling and receiving the results of the incubation.

Liquid impingers provide a versatile sampling platform for sampling biological particles, as well as molecular contamination. These devices work by flowing a gas (e.g. air, process gas or mixture of gases) through an absorbent material, such as a liquid absorbent material, which is exposed to the gas for a set time period, then removed for external testing, such as via incubation followed by inspection and/or chemical methods such as PCR, mass spectroscopy and/or chromatography, to identify, characterize and/or quantify contaminants that were present in the gas and transferred into the absorbent material. US Patent Publication US 2021/0063349, for example, provides impinger-based sampling systems using a real time analyzer to allowed for trigger detection and/characterization of contaminants in gas samples and environments upon meeting certain real time criteria.

Conventional impinger systems are susceptible to various drawbacks. For example, known impingers are usually made of glass and, thus, are not consumables (i.e., disposable), as they have to be washed and sterilized prior to each repeated use. This extra washing and sterilizing process introduces possible contamination, particularly when not performed satisfactorily. Moreover, known liquid impingers are often too big to be ideally located at the monitoring point, since large liquid impingers are necessary to contain enough volume of liquid growth media to mitigate evaporation caused by the sampling process.

Therefore, there remains a need for sampling systems and methods capable of achieving efficient sampling of viable biological particles. For example, particle collection systems are needed for cleanroom and manufacturing applications that provide high particle collection efficiencies while maintaining the viabilities of collected bioparticles. In addition, particle collection systems are needed for cleanroom and manufacturing applications that reduce the occurrence of false positive detection events.

SUMMARY

The invention generally provides devices and methods for sampling, detecting and/or characterizing analytes in a gas, such as particles and/or molecular analytes. In some embodiments, for example, invention provides devices and methods for sampling, collection and analysis of viable biological particles, such as microorganisms, and molecular contaminants. Devices and methods of the invention include impingers and bubblers for collecting and/or analyzing analytes, such as particles and/or molecular contaminants in manufacturing environments requiring low levels of contaminants, such as cleanroom and aseptic environments. Devices and methods of the invention include single use, impingers and bubblers capable of filling, sterilization, use and/or readout in a full-integrated configuration, in a manner to minimize, or entirely eliminate, risks associated with user handling, such as the occurrence of false positive determinations due to contamination during sampling, particle growth and/or or analysis processes. Devices and methods of the invention include single use, impingers and bubblers comprising polymer materials, for example, polymer materials capable of manufacture via molding, extrusion, vacuum forming, three-dimensional printing and subtractive manufacturing and/or polymer materials at least partially optically transparent in the visible spectral region.

In some aspects, disclosed herein is a liquid impinger, comprising:
  a vessel comprising a vertical axis, a top portion, an interior, and a bottom portion comprising an interior base,
  a gas inlet in fluid communication with the interior via at least one nozzle positioned in the interior and attached to the bottom portion, wherein the nozzle comprises a nozzle opening, and
  a gas outlet in fluid communication with the interior,
  wherein the gas inlet, the at least one nozzle, the interior, and the gas outlet sequentially define a gas flow path, and
  wherein the vessel is configured to contain a liquid within the interior.

In one embodiment, the vessel comprises a sampling port, the sampling port configured to provide selective access to the liquid in the interior of the vessel for sampling the liquid in the vessel. In one embodiment, the vessel comprises a removable cap for sealing the sampling port. In one embodiment, the cap comprises a septum, the septum being configured to receive a needle to allow a liquid to be withdrawn from the interior of the vessel while maintaining the interior of the vessel in a sealed state.

In some aspects, disclosed herein is a method comprising:
  providing a liquid impinger of any preceding aspect or providing a liquid impinger comprising:
    a vessel comprising a vertical axis, a top portion, an interior containing a liquid, and a bottom portion comprising an interior base,
    a gas inlet in fluid communication with the interior via at least one nozzle positioned in the interior and attached to the bottom portion, wherein the nozzle comprises a nozzle opening and the nozzle opening is submerged in the liquid, and
    a gas outlet in fluid communication with the interior,
    wherein the gas inlet, the at least one nozzle, the interior, and the gas outlet sequentially define a gas flow path,
  transporting a gas comprising analytes along the gas flow path and into contact with, and optionally through, the liquid, and
  transferring at least a portion of the analytes from the gas into the liquid, optionally wherein the analytes comprise particles, molecular analytes or a combination thereof, and further optionally for some embodiments wherein the analytes comprise biological particles.

In one embodiment, the method may comprise in response to the transferring step, removing a sample of the liquid from the interior of the vessel via a sample port. In one embodiment, the step of removing a sample comprises inserting a needle into a septum of the sample port.

In some aspects, disclosed is a method for producing a liquid impinger, the method comprising:
  forming at least two components of a liquid impinger,
  optionally, assembling the at least two components to produce an assembled liquid impinger, the assembled liquid impinger comprising:
    a vessel comprising a vertical axis, a top portion, an interior, and a bottom portion comprising an interior base,
    a gas inlet in fluid communication with the interior via at least one nozzle positioned in the interior and attached to the bottom portion, wherein the nozzle comprises a nozzle opening, and
    a gas outlet in fluid communication with the interior,
    wherein the gas inlet, the at least one nozzle, the interior, and the gas outlet sequentially define a gas flow path, and
    wherein the vessel is configured to contain a liquid within the interior,
  optionally, filling a portion of the interior of the assembled liquid impinger with the liquid to produce a filled liquid impinger,
  optionally, exposing the filled liquid impinger to radiation to sterilize at least a portion of the liquid present in the interior of the liquid impinger, thereby producing a filled and sterilized liquid impinger, and
  optionally, before or after the exposing step, packaging the filled liquid impinger or the filled and sterilized liquid impinger in a manner that prevents ingress of particles or contamination into the interior of the liquid impinger.

In some aspects, disclosed is a method for producing a filled and sterilized liquid impinger, the method comprising:
  forming at least two components of a liquid impinger, assembling the at least two components to produce an assembled liquid impinger, the assembled liquid impinger comprising:
  a vessel comprising a vertical axis, a top portion, an interior, and a bottom portion comprising an interior base,
  a gas inlet in fluid communication with the interior via at least one nozzle positioned in the interior and attached to the bottom portion, wherein the nozzle comprises a nozzle opening, and
  a gas outlet in fluid communication with the interior,
  wherein the gas inlet, the at least one nozzle, the interior, and the gas outlet sequentially define a gas flow path, and
  wherein the vessel is configured to contain a liquid within the interior,
filling a portion of the interior of the assembled liquid impinger with the liquid to produce a filled liquid impinger,
exposing the filled liquid impinger to radiation to sterilize at least a portion of the liquid present in the interior of the liquid impinger, thereby producing the filled and sterilized liquid impinger, and
optionally, before or after the exposing step, packaging the filled liquid impinger or the filled and sterilized liquid impinger in a manner that prevents ingress of particles or contamination into the interior of the liquid impinger.

In some aspects, disclosed is a method for producing a filled and sterilized liquid impinger, the method comprising:
  a first providing step, comprising providing a filled liquid impinger, wherein the filled liquid impinger comprises:
    a vessel comprising a vertical axis, a top portion, an interior, and a bottom portion comprising an interior base,
    a gas inlet in fluid communication with the interior via at least one nozzle positioned in the interior and attached to the bottom portion, wherein the nozzle comprises a nozzle opening, and
    a gas outlet in fluid communication with the interior,
    wherein the gas inlet, the at least one nozzle, the interior, and the gas outlet sequentially define a gas flow path, and
    wherein the vessel is contains a liquid within the interior,
  exposing the filled liquid impinger to radiation to sterilize at least a portion of the liquid present in the interior of the liquid impinger, thereby producing the filled and sterilized liquid impinger, and
  optionally, before or after the exposing step, packaging the filled liquid impinger or the filled and sterilized liquid impinger in a manner that prevents ingress of particles or contamination into the interior of the liquid impinger.

In some embodiments, the liquid impinger of the present systems and methods is a sampler, collector or analyzer for analytes such as particles and/or molecular analytes. In some embodiments, the liquid impinger of the present systems and methods is an impinger or a bubbler for sampling analytes such as particles and/or molecular analytes. In some embodiments, the method is for sampling, characterizing and/or monitoring analytes in a gas, optionally wherein the analytes comprising particles, such as biological particles or nonbiological particles, or molecular analytes, such as molecular contaminants, impurities, or process chemical, or any combination thereof.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

STATEMENTS REGARDING NOMENCLATURE

Figure 1:
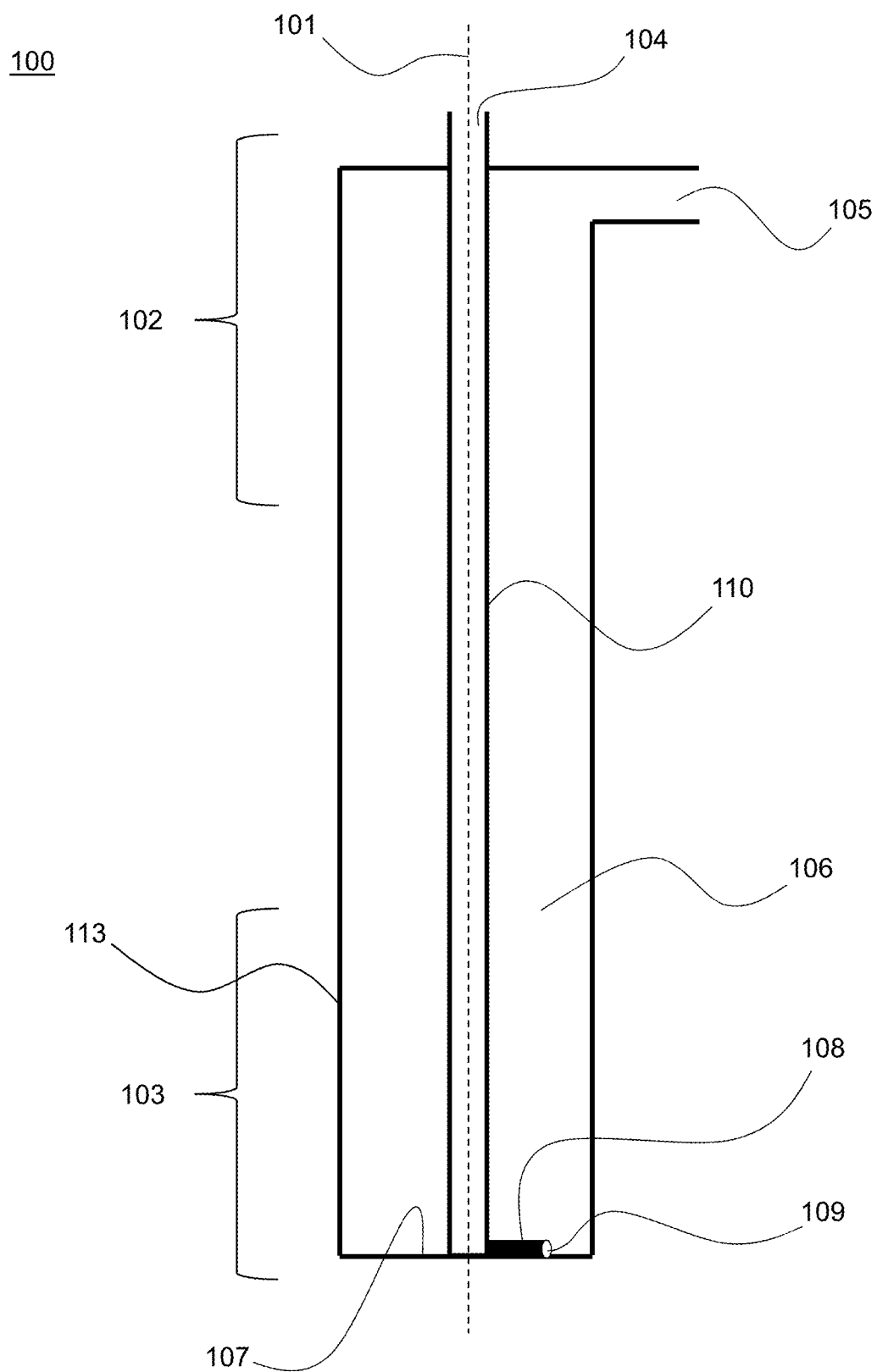
FIG. 1. depicts some aspects of a liquid impinger, in particular, a liquid impinger for sampling a gas, in which the nozzle is positioned in the interior and attached to the bottom portion, and in which the gas inlet is connected to the nozzle by a tube extending from the top portion to the bottom portion within the interior.

In general, the terms and phrases used herein have their art-recognized meaning, which can be found by reference to standard texts, journal references and contexts known to those skilled in the art. The following definitions are provided to clarify their specific use in the context of the invention.

As used herein "analyte" refers to one or more species, compositions or materials to be sampled, detected, monitored and/or analyzed. Analytes may refer to atomic, ionic, clusters and molecular species or may refer to particles, including biological and nonbiological particles. In some embodiments, analytes are trace components, impurities and/or contaminants of a gas, such as trace components, impurities and/or contaminants of a liquid, a gas or any mixtures thereof, including water, air, solvents, solutions, process liquid chemicals, process gases, gases or liquids from a manufacturing and/or processing environment or process. In an embodiment, analytes are in a gas undergoing monitoring, such as a gas or liquid from a sample, a process or an environment undergoing monitoring, such as a cleanroom or clean zone environment. In an embodiment, analytes are particles, optionally biological particles such as viable biological particles. In an embodiment, analytes are molecular analytes.

The term "particle" or "particles" refers to small objects which are often regarded as contaminants. A particle can be, but need not be, any material created by the act of friction, for example when two surfaces come into mechanical contact and there is mechanical movement. Particles can be single components, or composed of aggregates of material, such as dust, dirt, smoke, ash, water, soot, metal, oxides, ceramics, minerals, or any combination of these or other materials or contaminants. "Particles" may also refer to biological particles, for example, viruses, spores and microorganisms including bacteria, fungi, archaea, protists, other single cell microorganisms. Biological particles include, but are not limited to, microorganisms having a particle size of 0.1-20 µm. Biological particles include viable biological particles capable of reproduction, for example, upon incubation within a growth media. In some embodiments, for example, biological particles are characterized by a size dimension (e.g., effective diameter) ranging from 0.1 to 15 µm, optionally for some applications ranging from 0.5 to 5 µm. A particle may refer to a small object which may be collected, detected, characterized and/or identified via a particle sampler, collector or detector, such as an impinger, impactor, bubbler or particle counter. A particle may refer to any small object which absorbs or scatters light and is thus detectable by an optical particle counter. As used herein, "particle" or "particles" is intended to be exclusive of the individual atoms or molecules of a carrier gas or sample medium, for example, water, air, process liquid chemicals, process gases, nitrogen, oxygen, carbon dioxide, etc. In some embodiments, particles may be initially present on a surface, such as a tool surface in a microfabrication facility or production surface in a pharmaceutical fabrication facility, liberated from the surface and subsequently analyzed in a gas. Some embodiments of the present invention are capable of sampling, collecting, detecting, sizing, and/or counting particles comprising aggregates of material having a size greater than 50 nm, 100 nm, 1 µm or greater, or 10 µm or greater. In some embodiments, particles include particles having a size selected from 50 nm to 50 µm, a size selected from 100 nm to 10 µm, or a size selected from 500 nm to 5 µm.

The term "particle size," as used herein, refers to the average or effective diameter of particles, the average or effective length of particles, the average or effective width of particles, the equivalent spherical diameter (diameter of sphere of equivalent volume) of particles, or the largest dimension of a particle, as will be clear from context.

The expression "molecular analyte" refers to an analyte comprising atomic, ionic, clusters and molecular species. Molecular analytes include molecular contaminants, impurities, process chemicals, trace components, and the like. In an embodiment, molecular analytes comprises one or more acids, such as HF, HCl, HBr, $HNO_3$, $H_2SO_4$, $H_3PO_4$, HCOOH and $CH_3COOH$, or any combination of these. In an embodiment, molecular analytes comprises one or more bases, such as $NH_3$, methylamine, dimethylamine, ethylamine and N-methyl-2-pyrrolidone, or any combination of these. In an embodiment, molecular analytes comprises one or more volatile organic compounds, such as $CH_3OH$, isopropyl alcohol, propylene glycol monomethyl ether acetate (PGMEA) and hexamethyl disilazane or any combination of these.

As used herein, "impinger" refers to a container, passage or vessel for receiving a gas, wherein analytes in the gas are contacted with an impinger medium so as to capture, collect and/or transform analytes. Impingers useful for the present systems and methods may house, or otherwise incorporate, a range of impinger media for capturing, collecting and/or transforming analytes including one or more liquids (including solutions), gels and/or sols. In some embodiments, an impinger is a "bubbler," for example, a device in which the gas flows through the impinger as to agitate or bubble the liquid therein, such as a solution or solvent. In some embodiments, impingers include impinger media comprising a layer, a film, droplets or matrix of liquid, solution, sol and/or gel material. Impingers may be made from anti-leeching materials, to reduce the generation of species that may interfere with subsequent detection and/or analysis of collected, captured or transformed analytes, such as ions, molecules or particle arising from the impinger itself or components thereof.

The expression "sampling a particle" broadly refers to collection of particles in a gas flow, for example, from an environment undergoing monitoring. Sampling in this context includes transfer of particles in a gas flow to a collector, collection media and/or growth media, for example, the liquid media of a impinger or bubbler, or an impact surface of an impactor. Alternatively, sampling may refer to transporting particles in a gas through a particle analysis region, for example, for optical detection and/or characterization. Sampling may refer to collection of particles having one or more preselected characteristics, such as size (e.g., cross sectional dimension such as diameter, effective diameter, etc.), particle type (biological or nonbiological, viable or nonviable, etc.) or particle composition. Sampling may optionally include analysis of collected particles, for example, via subsequent optical analysis, imaging analysis or visual analysis. Sampling may optionally include growth of viable biological particles, for sample, via an incubation process involving a growth medium. A sampler refers to a device for sampling analytes such as particles and/or molecular analytes.

The expression "detecting a particle" broadly refers to sensing, identifying the presence of and/or characterizing a particle. In some embodiments, detecting a particle refers to counting particles. In some embodiments, detecting a particle refers to characterizing and/or measuring a physical characteristic of a particle, such as diameter, cross sectional dimension, shape, size, aerodynamic size, or any combination of these. In some embodiments, detecting a particle refers to visualizing, visually counting and/or optically imaging a particle. A particle counter is a device for counting the number of particles in a gas or volume of gas, and optionally may also provide for characterization of the particles, for example, on the basis of size (e.g., cross sectional dimension such as diameter or effective diameter), particle type (e.g. biological or nonbiological), or particle composition. An optical particle counter is a device that detects particles by measuring scattering, emission or absorbance of light by particles.

The term "polymeric material" refers to a macromolecule composed of repeating structural units connected by covalent chemical bonds or the polymerization product of one or more monomers, often characterized by a high molecular weight. The term "polymeric material" includes homopolymers, or polymers consisting essentially of a single repeating monomer subunit. The term "polymeric material" also includes copolymers, or polymers consisting essentially of two or more monomer subunits, such as random, block, alternating, segmented, grafted, tapered and other copolymers. As used herein, the term "polymeric material" does not include glass or ceramic.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyimide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

Figure 7A:
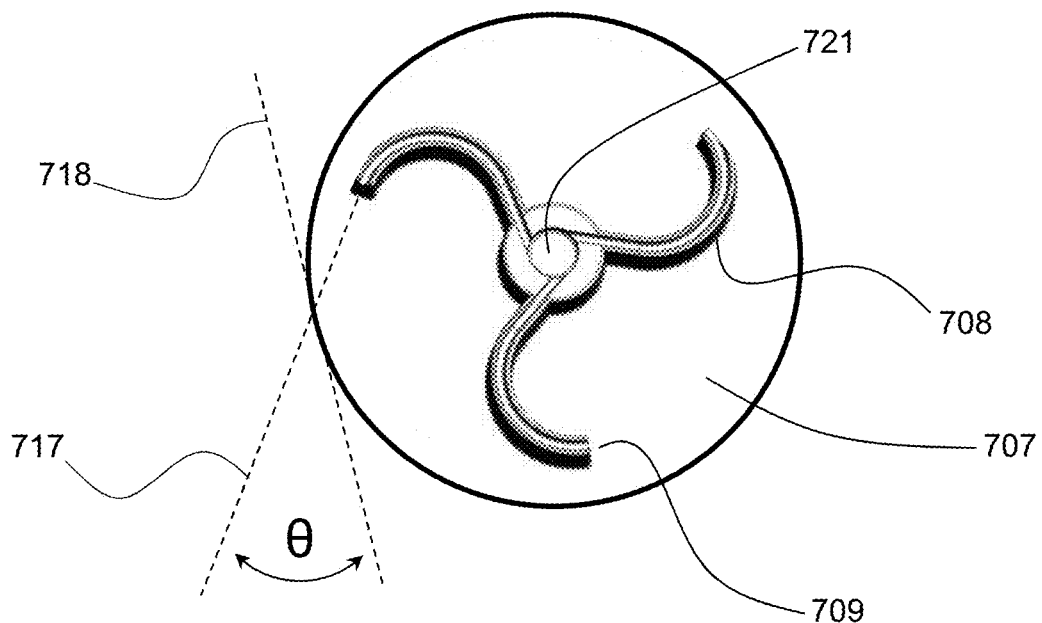
FIGS. 7A-7B. depict aspects of nozzle configuration and helps aid in understanding the definition of the term "horizontal angle," as described elsewhere herein.
Figure 7B:
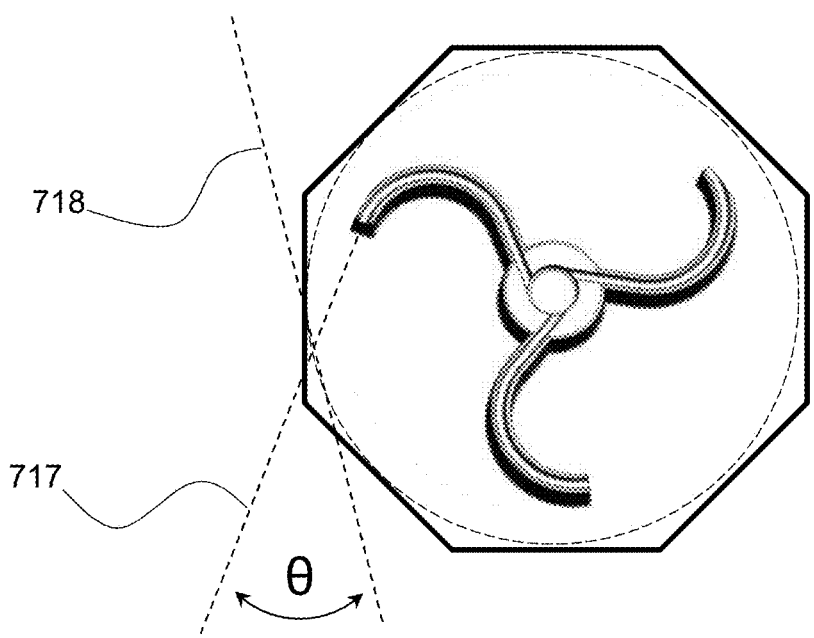

The term "horizontal angle" ($\theta$) refers to the angle formed between (1) the horizontal component of the nozzle direction when viewed along the vertical axis and (2) the tangent line where the horizontal component of the nozzle direction intersects the side wall. The nozzle direction only includes its horizontal component; in other words, to the extent the nozzle is angled up or down along the vertical axis, such vertical component is not considered when determining the horizontal angle. Reference to FIG. 7A is useful to understand the meaning of "horizontal angle" ($\theta$). In this regard, the horizontal component of the nozzle direction 717 is determined by viewing the nozzle along the vertical axis from the perspective from the top portion to the bottom portion (as shown in FIG. 7A), placing an imaginary plane perpendicular to the vertical axis (i.e., horizontal plane) that passes through the center of the nozzle opening, and drawing a line in this horizontal plane representing the horizontal component of the nozzle direction (feature 717). In addition, the location where this horizontal plane passes through the side wall is the relevant portion of the side wall for determining the tangent line 718, not where the nozzle direction would actually intersect the side wall considering any vertical component or gas velocity. The angle between the horizontal component of the nozzle direction 717 and the tangent line 718 in this horizontal plane is the horizontal angle $\theta$. This definition is appropriate for spherical, cylindrical, ellipsoidal, and other curved side walls. In situations where the side wall is a different shape, such as polygonal, the tangent line is determined relative to the smallest circle that fits within the polygonal or other shape, as depicted in FIG. 7B. The other features of FIG. 7B are the same as in FIG. 7A. It should be noted that FIGS. 7A and 7B, while useful for understanding the concept of the "horizontal angle," are not drawn to mathematical precision, and thus certain features, such as the tangent lines, are not necessarily depicted as perfect tangent lines and thus such depictions should be considered illustrative only.

Figure 8:
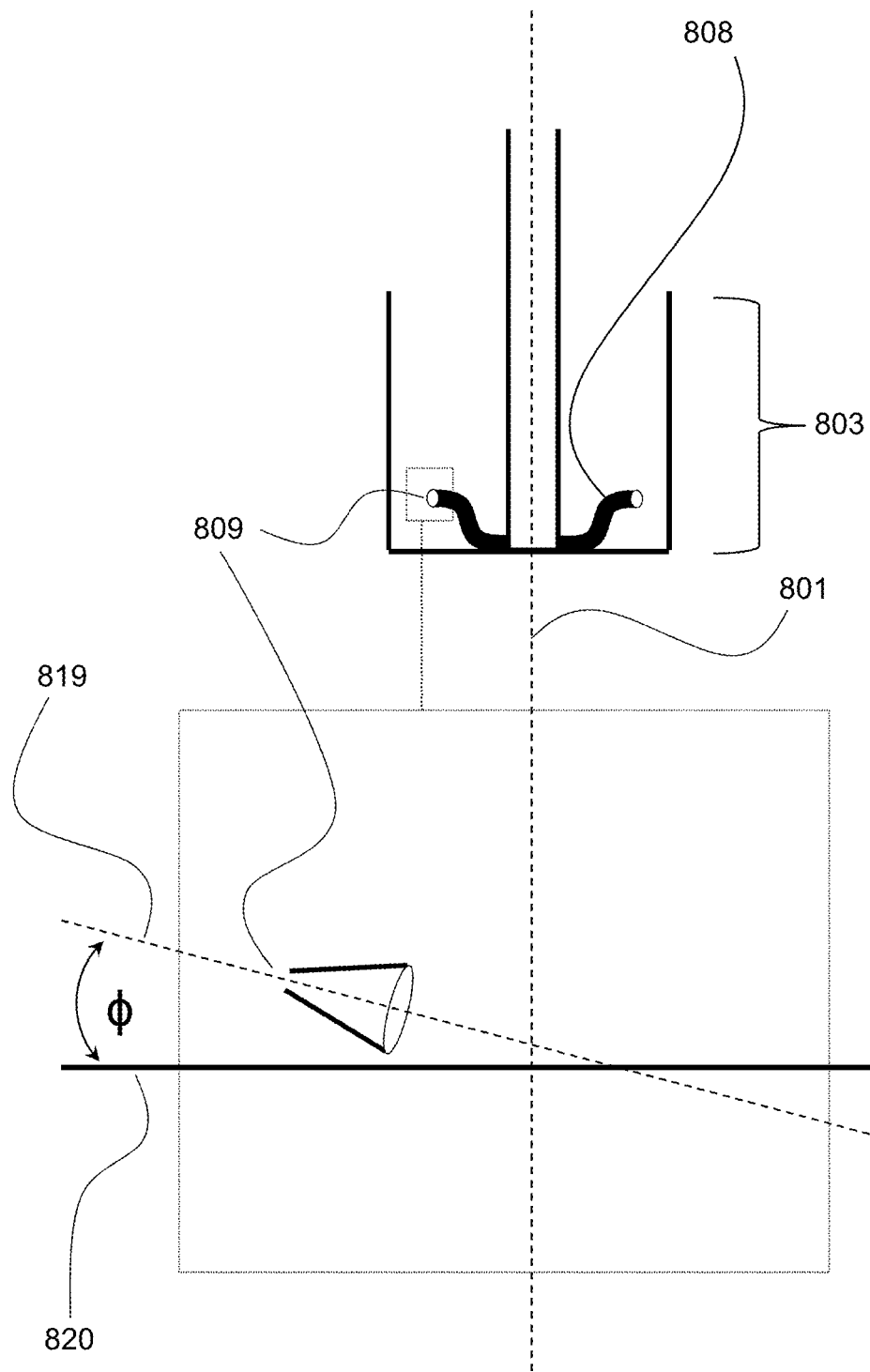
FIG. 8. depicts aspects of nozzle configuration and helps aid in understanding the definition of the term "vertical angle," as described elsewhere herein.

The term "vertical angle" ($\phi$) refers to the angle formed between the plane perpendicular to the vertical axis (i.e., horizontal plane) and the nozzle direction when viewed from the direction that is perpendicular to the vertical axis and perpendicular to the nozzle direction. FIG. 8 is useful for understanding the vertical angle ($\phi$). FIG. 8 depicts bottom portion 803, nozzle 808, nozzle opening 809, vertical axis 801, and horizontal plane 820 that is perpendicular to vertical axis 801. To better show the detail of the vertical angle, FIG. 8 shows a blow-up of the nozzle/nozzle opening and nozzle direction. The nozzle 808 is viewed from a direction perpendicular to vertical axis 801 and perpendicular to nozzle direction 819. The angle ($\phi$) formed between plane 820 and nozzle direction 819 when viewed from this perspective is the "vertical angle" ($\phi$). Positive vertical angles indicate the nozzle direction is pointed toward the top portion (i.e., above the horizontal plane), negative vertical angles indicate the nozzle direction is pointed away from the top portion (i.e., below the horizontal plane), and a vertical angle of 0 degrees indicates the nozzle direction is within the horizontal plane (i.e., not pointing toward or away from the top portion). As in FIGS. 7A and B, the features of FIG. 8 are not drawn with mathematical precision, and thus depictions in FIG. 8 should be considered illustrative only.

"Fluid communication" refers to the arrangement of two or more objects such that a gas can be transported to, past, through or from one object to another. For example, in some embodiments two objects are in fluid communication with one another if a gas flow path is provided directly between the two objects. In some embodiments, two objects are in fluid communication with one another if a gas flow path is provided indirectly between the two objects, such as by including one or more other objects or flow paths between the two objects. For example, in one embodiment, the following components of a particle impinger are in fluid communication with one another: such as one or more of gas inlet, a gas outlet, interior, nozzle, tube, opening a flow restriction, a pressure sensor, a flow generating device. In one embodiment, two objects present in a body of gas are not necessarily in fluid communication with one another unless gas from the first object is drawn to, past and/or through the second object, such as along a flow path.

"Flow rate" refers to an amount of gas flowing past a specified point or through a specified area, such as through intake apertures or a gas outlet of a particle impinger or bubbler. In one embodiment a flow rate refers to a mass flow rate, i.e., a mass of the gas flowing past a specified point or through a specified area. In one embodiment, a flow rate is a volumetric flow rate, i.e., a volume of the gas flowing past a specified point or through a specified area.

When disclosing numerical values herein, for example, 1, 2, 3, 4, 5, 6, 7, 8, 9, 10, the following sentence typically follows such numerical values: "Each of the foregoing numbers can be preceded by the term 'about,' 'at least,' 'at least about,' 'less than,' or 'less than about,' and any of the foregoing numbers can be used singly to describe a single point or an open-ended range, or can be used in combination to describe multiple single points or a close-ended range." This sentence means that each of the aforementioned numbers can be used alone (e.g., 4), can be prefaced with the word "about" (e.g., about 8), prefaced with the phrase "at least about" (e.g., at least about 2), prefaced with the phrase "at least" (e.g., at least 10), prefaced with the phrase "less than" (e.g., less than 1), prefaced with the phrase "less than about" (e.g., less than about 7), or used in any combination with or without any of the prefatory words or phrases to define a range (e.g., 2 to 9, about 1 to 4, at least 3, 8 to about 9, 8 to less than 10, about 1 to about 10, and so on). Moreover, when a range is described as "about X or less," this phrase is the same as a range that is a combination of "about X" and "less than about X" in the alternative. For example, "about 10 or less" is the same as "about 10, or less than about 10." Such interchangeable range descriptions are contemplated herein. Other range formats may be disclosed herein, but the difference in formats should not be construed to imply that there is a difference in substance.

As used herein, the term "about" means that slight variations from a stated value may be used to achieve substantially the same results as the stated value. In circumstances where this definition cannot be applied or is exceedingly difficult to apply, then the term "about" means a 10% deviation (plus or minus) from the stated value.

DETAILED DESCRIPTION

In the following description, numerous specific details of the devices, device components and methods of the present invention are set forth in order to provide a thorough explanation of the precise nature of the invention. It will be apparent, however, to those of skill in the art that the invention can be practiced without these specific details.

The liquid impinger and bubbler liquid impingers, systems, and methods disclosed herein provide various benefits. For example, the use of a liquid medium permits easier detection of particles, such as microorganisms, with less handling (and thus less risk of contamination from human contact), as well as faster growth of such microorganisms during an incubation step. In addition, the use of a sterilized closed device, which may be disposable, minimizes or prevents false positives. Moreover, the liquid impinger designs and methods of use do not destroy microorganisms through fast velocity gas flow, and such designs and methods minimize loss of liquid during sampling, allowing a lengthened monitoring time while minimizing the liquid impinger dimensions. For example, use of multiple nozzles allows a larger overall gas flow, but a lower gas velocity for each nozzle, so as to prevent microorganism death or nonviability. Moreover, in some aspects, certain features of the nozzles, such as the nozzle angles and dimensions, maximize gas/liquid interaction time by way of imparting a swirl into the liquid by employing a large horizontal velocity component to the gas flow, and a minimized vertical velocity component to the gas flow, thereby transferring a relatively large amount of particles from the gas into the liquid. In addition, in some aspects, the nozzle designs, either alone or in conjunction with the liquid impinger wall designs, reduce loss of liquid through evaporation, allowing a smaller working volume of the liquid during operation of the liquid impinger, and thus an overall smaller liquid impinger size, facilitating placement in sampling locations having space limitations.

In some aspects, disclosed herein is a liquid impinger, comprising:
    a vessel comprising a vertical axis, a top portion, an interior, and a bottom portion comprising an interior base,
    a gas inlet in fluid communication with the interior via at least one nozzle positioned in the interior and attached to the bottom portion, wherein the nozzle comprises a nozzle opening, and
    a gas outlet in fluid communication with the interior,
    wherein the gas inlet, the at least one nozzle, the interior, and the gas outlet sequentially define a gas flow path, and
    wherein the vessel is configured to contain a liquid within the interior.

In some aspects, the liquid impinger is comprised of any suitable material. In some aspects, the material comprises, consists of, or consists essentially of at least one polymeric material. In some aspects, the polymeric material includes organic polymers that may be in amorphous, semi-amorphous, crystalline or partially crystalline states. Cross-linked polymers are particularly useful for some applications. Polymers useable in the methods, systems, liquid impingers, devices, and components include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile, poly(acrylonitrile-butadiene-styrene), polyimide-imide polymers, polyimides, acrylic, polyacrylates, polybenzimidazole, polybutylene, polycarbonate, polyesters, polyetherimide, polyethylene, polyethylene copolymers and modified polyethylenes, polyketones, poly (alkyl)(alkyl)acrylates (such as poly(methylmethacrylate),) polymethylpentene, polyphenylene oxides and polyphenylene sulfides, polyphthalamide, polypropylene, polyurethane (e.g., thermoplastic polyurethane), transparent polystyrene (e.g., Polystyrol™ available from BASF), polystyrene, high impact polystyrene, styrenic resins, sulfone-based resins, vinyl-based resins, rubber (including natural rubber, thermoplastic rubber, styrene-butadiene, polybutadiene, neoprene, ethylene-propylene, butyl, nitrile, silicones), polyvinyl chloride, polyoxymethylene, polyolefin or any combinations of these. In some aspects, the polymeric material comprises poly(acrylonitrile-butadiene-styrene), polyethylene, polycarbonate, polyamide (nylon), polystyrene, transparent polystyrene (e.g., Polystyrol™ available from BASF), high impact polystyrene, polypropylene, polyoxymethylene, polyurethane (e.g., thermoplastic polyurethane), rubber (e.g., thermoplastic rubber), or any combination thereof. In some aspects, the liquid impinger does not comprise glass or ceramic. In some aspects, the liquid impinger is not made a material comprising glass or ceramic. In some aspects, at least a portion of the liquid impinger comprises glass or ceramic.

In some aspects, various benefits are associated with a liquid impinger comprising, consisting of, or consisting essentially of at least one polymeric material, or a liquid impinger formed from at least one polymeric material. Such benefits include, for example, (1) transparency of the polymeric material to radiation for the purposes of sterilization of at least a portion of the interior of the liquid impinger (and/or at least a portion of any liquid contained therein), (2) ability of the liquid impinger to be manufactured, for example, via molding, extrusion, additive manufacturing, or subtractive manufacturing, which allows for mass production, as well as fine detail of the produced liquid impinger in terms of positioning and structure of, for example, the nozzles, (3) inertness of the polymeric material (e.g., to not detrimentally affect or kill any biological particles transferred from the gas into the liquid therein), (4) disposability of the liquid impinger (e.g., via recycling or disposal in a landfill), (5) cost effectiveness (e.g., costs associated with purchasing polymeric materials and/or forming into the liquid impinger via, for example, molding, are less expensive than glass or ceramic materials and the processes required to form glass or ceramic into a desired shape with associated nozzles in appropriate positions with desired detail, or (6) any combination thereof. In any event, in some aspects, a liquid impinger comprises glass and/or ceramic.

In some aspects, the liquid impinger comprises any suitable amount of polymeric material. In some aspects, the liquid impinger comprises polymeric material in an amount (wt. %) of 50, 55, 60, 65, 70, 75, 80, 81, 82, 83, 84, 85, 86, 87, 88, 89, 90, 91, 92, 93, 94, 95, 96, 97, 98, 99, or 100. Each of the foregoing numbers can be preceded by the word "about," "at least," "at least about," "less than," or "less than about," and any of the foregoing numbers can be used singly to describe a single point or an open-ended range, or can be used in combination to describe multiple single points or a close-ended range. For example, in some aspects, the liquid impinger comprises polymeric material in an amount (wt. %) of at least 50, 75 to 98, at least 90, or 65 to 88.

In some aspects, the liquid impinger further comprises the liquid. In some aspects, the liquid is a liquid growth medium. In some aspects, the liquid comprises, consists of, or consists essentially of water. In some aspects, the liquid (e.g., liquid growth medium) is or comprises, consists of, of consists essentially of tryptic soy broth (TSB), oil, mineral oil, VIATRAP available from SKC, Inc, R2A broth available from HIMEDIA, or any combination thereof. In some aspects, the liquid further comprises an additive. In some aspects, the additive is or comprises a surfactant, an anti-foaming agent, or a combination thereof. In some aspects, the additive is or comprises lecithin. In some aspects, the additive is or comprises an anti-foaming agent. In some aspects, the liquid comprises an anti-foaming agent. In some aspects, the anti-foaming agent is C16-C18 ethoxylated propoxylated alcohols (e.g., CAS #68002-96-0, or CPL 2908 from Silitex, SRL). In some aspects, the anti-foaming agent (e.g., C16-C18 ethoxylated propoxylated alcohols) is employed in the liquid in an amount of 0.001 vol. % to 1 vol. % (e.g., 0.001 vol. % to 0.01 vol. %, 0.01 vol. % to 0.1 vol. %, 0.1 vol. % to 0.5 vol. %, or 0.5 vol. % to 1 vol. %). In some aspects, the surfactant is an ionic surfactant, a nonionic surfactant, or a combination thereof. In some aspects, the surfactant is TWEEN, such as TWEEN 80, or a polysorbate, such as polysorbate 20, 40, 60, 80, or any combination thereof. In some aspects, the liquid comprises VIATRAP available from SKC, Inc. In some aspects, the liquid comprises TSB, lecithin, and TWEEN 80. In some aspects, the liquid comprises R2A broth. In some aspects, the liquid impinger does not contain the liquid (e.g., when manufactured, shipped, and/or sold to the end user, prior to filling with a liquid).

In some aspects, the liquid employed in the liquid impinger does not form an emulsion when gas is passed through the liquid impinger along the gas flow path, for example, when bubbling the gas (e.g., air or sample gas) through the liquid. In some aspects, an emulsion can be prevented from forming by the use of one or more surfactants and/or anti-foaming agents.

In some aspects, such as when the liquid impinger contains the liquid, the at least one nozzle is submerged in the liquid, and transporting a gas along the gas flow path causes the gas to pass through the liquid. In some aspects, positioning the at least one nozzle in the bottom portion of the liquid impinger maximizes the flow path through the liquid impinger of a gas comprising particles, which maximizes the gas/liquid interaction time, thereby maximizing the amount of particles transferred from the gas into the liquid. In some aspects, the gas comprises particles. In some aspects, the particles comprise at least one microorganism or virus. In some aspects, the particles comprise bacteria, spores, or a combination thereof. In some aspects, the at least one nozzle is attached to the bottom portion (e.g., via the interior base, a side wall, or a combination thereof). In some aspects, the at least one nozzle is not attached to the bottom portion directly, but is attached indirectly to the bottom portion, e.g., by way of a tube or other feature. In some aspects, the at least one nozzle is not attached to the bottom portion. In some aspects, the at least one nozzle is not attached to the bottom portion, and the gas inlet is connected to the at least one nozzle by a tube extending from the top portion to the bottom portion within the interior. In some aspects, the at least one nozzle is not attached to the bottom portion, and the gas inlet is connected to the at least one nozzle by a tube not located within the interior, but rather via a tube that approaches the bottom portion from the side or below.

In some aspects, the liquid impinger is produced by any suitable process. In some aspects, the liquid impinger is produced by a process comprising molding, injection molding, blow molding, rotational molding, additive manufacturing, three-dimensional printing, subtractive manufacturing, casting, forming, vacuum forming, extrusion, or any combination thereof, and, optionally, wherein the process produces at least three separate components that are joined together to form the liquid impinger. In some aspects, the process comprises injection molding. In some aspects, the process comprises additive manufacturing, such as three-dimensional printing. In some aspects, the process comprises injection molding and additive manufacturing.

In some aspects, the liquid impinger comprises any components. In some aspects, the liquid impinger comprises at least three separate components that are joined together to form the liquid impinger. In some aspects, the liquid impinger comprises three components, for example, a bottom portion, a base, and a third component comprising the top portion. In some aspects, the liquid impinger comprises four, five, six, or seven components. In some aspects, the liquid impinger comprises one or more caps configured to attach to each of the gas inlet and gas outlet. In some aspects, the one or more caps are in position on the gas inlet and gas outlet prior to and/or after use of the liquid impinger for gas sampling so as to prevent contamination from unwanted air from entering the liquid impinger.

In some aspects, the liquid impinger can be assembled from two or more components in any suitable fashion. In some aspects, the bottom portion is configured to be attached to or removed from the liquid impinger by rotating the bottom portion of the liquid impinger along threads in a screwing fashion. In some aspects, the two or more components (e.g., comprising the bottom portion) is configured to be attached to the liquid impinger via sliding (e.g., to form a snug fit), snapping, clicking, or any other suitable method.

In some aspects, such attachment is followed by securing the components in their attached configuration using heat (e.g., melting), glue, or a combination thereof.

In some aspects, the liquid impinger comprises any suitable number of nozzles. In some aspects, the liquid impinger comprises at least one nozzle. In some aspects, the at least one nozzle comprises at least two nozzles, at least three nozzles, at least four nozzles, at least five nozzles, at least six nozzles, or at least seven nozzles. In some aspects, the liquid impinger comprises two, three, four, five, six, or seven nozzles. In some aspects, the liquid impinger comprises three nozzles.

In some aspects, a nozzle can have a nozzle opening of any suitable size. In some aspects, a nozzle opening has a diameter (mm) of 0.01, 0.05, 0.1, 0.2, 0.3, 0.4, 0.5, 0.6, 0.7, 0.8, 0.9, 1, 1.2, 1.4, 1.6, 1.8, 2, 2.2, 2.4, 2.6, 2.8, 3, 3.2, 3.4, 3.6, 3.8, 4, 4.5, or 5. Each of the foregoing numbers can be preceded by the word "about," "at least," "at least about," "less than," or "less than about," and any of the foregoing numbers can be used singly to describe a single point or an open-ended range, or can be used in combination to describe multiple single points or a close-ended range. For example, in some aspects, a nozzle has a diameter of 0.1 to 3.2, 0.05 to 2.8, or less than 2.6. If the liquid impinger has multiple nozzles, each nozzle can have the same diameter, or each nozzle can have a different diameter. In instances where the nozzle opening is not circular, the numbers above refer to the diameter of the smallest circle that encompasses the opening.

In some aspects, a nozzle can have any suitable shape. In some aspects, the at least nozzle comprises a shape comprising an arc. In some aspects, the nozzle shape refers to the shape of the nozzle within the interior of the liquid impinger. For example, in some aspects, the at least one nozzle is attached to a tube extending from the top portion to the bottom portion within the interior, and the shape of the nozzle refers to the shape of the portion of the nozzle that extends from the tube to the nozzle opening. In some aspects, the shape of the nozzle is determined as viewed along the vertical axis. In some aspects, the at least one nozzle comprises a shape comprising an arc, and the arc is substantially within a plane that makes an angle with the vertical axis of 85 degrees to 95 degrees, or 80 degrees to 100 degrees, or about 90 degrees, or 90 degrees. In some aspects, a nozzle in the shape of an arc avoids forcefully impacting a gas flow exiting the nozzle opening directly into a side wall (e.g., at an angle of 90 degrees or 80-100 degrees), but rather promotes a swirling motion of a liquid within the interior, with the gas flow impacting the side wall at a relatively shallow angle. In some aspects, if the plane meets one or more of these angles, the vertical component of gas flow is minimized, which promotes swirling of the liquid and lengthening of the gas/liquid interaction time, rather than angling the gas flow toward the surface of the liquid or toward the interior base.

In some aspects, the gas inlet is connect to the at least one nozzle in any suitable manner. In some aspects, the gas inlet is connected to the at least one nozzle by a tube extending from the top portion to the bottom portion within the interior. In some aspects, the gas inlet is connected to the at least one nozzle by a tube that does not extend from the top portion to the bottom portion within the interior. For example, in some aspects, the gas inlet is connected to the at least one nozzle by a tube that approaches or is attached to the bottom portion, but such tube is not located within the interior of the liquid impinger. In some aspects, the gas inlet is connected to the at least one nozzle by a tube located underneath, to the side, or both, of the bottom portion of the liquid impinger.

In some aspects, the tube can have any suitable shape, for example, including straight, curved, spiral, substantially straight, substantially curved, substantially spiral, or any combination thereof. In some aspects, the tube shape is relative to the vertical axis. In some aspects, the tube is substantially straight along the vertical axis. In some aspects, the tube is substantially spiral along the vertical axis. In some aspects, the tube is substantially curved.

In some aspects, the gas flow path bends at any suitable angle between the tube and the at least one nozzle. For example, in some aspects, the gas flow path bends at an angle of X degrees between the tube and the at least one nozzle, in which X (degrees) is 75, 80, 85, 90, 95, 100, or 105. Each of the foregoing numbers can be preceded by the word "about," "at least," "at least about," "less than," or "less than about," and any of the foregoing numbers can be used singly to describe a single point or an open-ended range, or can be used in combination to describe multiple single points or a close-ended range. For example, in some aspects, the gas flow path bends at an angle of 80 degrees to 100 degrees, 75 to 105, or at least 85, between the tube and the at least one nozzle.

In some aspects, the nozzle opening has any suitable shape. In some aspects, the nozzle opening shape is circular, oval, triangular, rectangular, pentagonal, hexagonal, polygonal, star, or irregular. When a liquid impinger employs more than one nozzle, each nozzle can have a nozzle opening with the same or a different shape. For example, in some aspects, a liquid impinger comprises two or more nozzles, and each nozzle opening of the two or more nozzles is the same, e.g., a circular shape. In some aspects, a liquid impinger comprises two or more nozzles, and each nozzle opening of the two or more nozzles is different, e.g., one nozzle opening is oval and one nozzle opening is polygonal. All combinations of nozzle shapes are contemplated herein.

In some aspects, the at least one nozzle has any suitable horizontal angle ($\theta$). In some aspects, the horizontal angle ($\theta$) (degrees) is 0, 2, 4, 6, 8, 10, 12, 14, 16, 18, 20, 22, 24, 26, 28, 30, 32, 34, 36, 38, 40, 42, 44, 45, 46, 48, or 50. Each of the foregoing numbers can be preceded by the word "about," "at least," "at least about," "less than," or "less than about," and any of the foregoing numbers can be used singly to describe a single point or an open-ended range, or can be used in combination to describe multiple single points or a close-ended range. For example, in some aspects, the horizontal angle ($\theta$) (degrees) is 0 to 40, less than 45, 4 to 24, or 10 to 30. In some aspects, when there are multiple nozzles, each nozzle independently can have any of the aforementioned horizontal angles, such that each nozzle can have the same or different horizontal angle.

In some aspects, the at least one nozzle has any suitable vertical angle ($\phi$). In some aspects, the vertical angle ($\phi$) (degrees) is −45, −44, −42, −40, −38, −36, −34, −32, −30, −28, −26, −24, −22, −20, −18, −16, −14, −12, −10, −8, −6, −4, −2, 0, 2, 4, 6, 8, 10, 12, 14, 16, 18, 20, 22, 24, 26, 28, 30, 32, 34, 36, 38, 40, 42, 44, or 45. Each of the foregoing numbers can be preceded by the word "about," "at least," "at least about," "less than," or "less than about," and any of the foregoing numbers can be used singly to describe a single point or an open-ended range, or can be used in combination to describe multiple single points or a close-ended range. For example, in some aspects, the vertical angle ($\phi$) (degrees) is −40 to 40, 0, −10 to 0, 0 to 10, 8 to 18, or −6 to 6. In some aspects, when there are multiple nozzles, each nozzle independently can have any of the aforementioned vertical angles, such that each nozzle can have the same or different vertical angle.

In some aspects, the at least one nozzle has any suitable combination of horizontal angle ($\theta$) and vertical angle ($\phi$). Any vertical angle disclosed herein can be combined with any horizontal angle disclosed herein to form a combination. For example, in some aspects, the horizontal angle (degrees) is 0 to 45 and the vertical angle (degrees) is −40 to 40; the horizontal angle (degrees) is 0 to 30 and the vertical angle is −10 to 10; or the horizontal angle (degrees) is 4 to 34 and the vertical angle is 0 to 12.

In some aspects, the bottom portion further comprises a side wall. In some aspects, the side wall is a cylindrical, spherical, ellipsoidal, or polygonal shape described elsewhere herein. In some aspects, the bottom portion further comprises a side wall, and the nozzle opening is positioned within a suitable distance of the side wall. In some aspects, the bottom portion further comprises a side wall, and the nozzle opening is positioned substantially flush with the side wall. As used herein, "flush" with the side wall refers to a situation in which a surface that defines the nozzle opening is shared with the size wall of the bottom portion. Accordingly, a nozzle opening that is "substantially flush" with the side wall includes this "flush" situation, but also includes aspects where the nozzle opening is separated from the side wall by an exceedingly small and insignificant distance. In some aspects, the nozzle opening is positioned within a distance (mm) of X of the side wall, in which X is 0, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, or 20. Each of the foregoing numbers can be preceded by the word "about," "at least," "at least about," "less than," or "less than about," and any of the foregoing numbers can be used singly to describe a single point or an open-ended range, or can be used in combination to describe multiple single points or a close-ended range. For example, in some aspects, the distance (mm) is 0 to 10, 0 to 5, 1.5 to 12.5, less than 10, or less than 8. In some aspects, the bottom portion further comprises a side wall, and the nozzle opening is positioned within 10 mm of the side wall or substantially flush with the side wall.

In some aspects, the bottom portion of the liquid impinger can comprise any suitable shape. For example, in some aspects, the bottom portion comprises a cylindrical wall extending substantially along at least a portion of the vertical axis. In some aspects, the bottom portion is cylindrical. In some aspects, the bottom portion comprises a substantially spherical or ellipsoidal shape. In some aspects, the bottom portion comprises a bulb or round bottom shape. In some aspects, the bottom portion comprises a polygonal shape. In some aspects, the bottom portion comprises a polygonal shape that extends substantially along at least a portion of the vertical axis.

In some aspects, the interior comprises an interior base. In some aspects, the interior base can have any suitable shape. In some aspects, the interior base, in a direction perpendicular to the vertical axis, is flat or substantially flat. In some aspects, the interior base is convex, concave, spherical, or ellipsoidal. In some aspects, the interior base is pyramidal.

In some aspects, the liquid impinger further comprise at least one expanded portion between the bottom portion and the top portion, wherein the expanded portion has a larger internal cross-sectional area at its widest point than an internal cross-sectional area of the bottom portion at its widest point. In some aspects, the at least one expanded portion is a substantially spherical or ellipsoidal shape. In some aspects, the at least one expanded portion has a triangular or polygonal shape (when viewed from the direction perpendicular to the vertical axis or from the direction along the vertical axis). In some aspects, an internal cross-sectional area of the expanded portion becomes wider and then becomes narrower in a direction along the vertical axis from the bottom portion to the top portion. In some aspects, at least two or at least three expanded portions are present. In some aspects, the at least one expanded portion presents a surface that at least a portion of any evaporating liquid can impact, condense on, and return to the liquid in the bottom portion of the liquid impinger. In some aspects, the at least one expanded portion presents a surface that inhibits evaporation. In some aspects, the at least one expanded portion presents a surface that inhibits evaporation and breaks bubbles flowing toward the outlet. In some aspects, the at least one expanded portion is immediately above (in the direction of the top portion) and connected to the bottom portion.

In some aspects, the liquid impinger further comprises at least one tapered portion between the expanded portion and the top portion, wherein the at least one tapered portion tapers to a smaller internal cross-sectional area along the vertical axis toward the top portion. In some aspects, at least two or at least three tapered portions are present. In some aspects, the at least one tapered portion presents a surface that at least a portion of any evaporating liquid can impact, condense on, and return to the liquid in the bottom portion of the liquid impinger. In some aspects, the at least one tapered portion presents a surface that inhibits evaporation. In some aspects, the at least one tapered portion presents a surface that inhibits evaporation and breaks bubbles flowing toward the outlet. In some aspects, the at least one tapered portion is immediately above (in the direction of the top portion) and connected to the at least one expanded portion or the substantially straight-walled portion. In some aspects, the tapered portion tapers gradually, whereas in some aspects the tapered portion tapers quickly or sharply.

In some aspects, the liquid impinger further comprises at least one substantially straight-walled portion between the expanded portion and the tapered portion. For example, the substantially straight-walled portion is substantially straight relative to the vertical axis. In some aspects, the at least one substantially straight-walled portion is substantially cylindrical. In some aspects, at least two or at least three substantially straight-walled portions are present (e.g., along the length of the vertical axis). In some aspects, the at least one tapered portion is immediately above (in the direction of the top portion) and connected to the at least one expanded portion or the substantially straight-walled portion. In some aspects, the substantially straight-walled portion has a smaller (or larger) internal cross-sectional area at its widest point than the cross-sectional area of the bottom portion at its widest point.

In some aspects, the liquid impinger further comprises a shelf or roof. In some aspects, the shelf or roof comprises a surface perpendicular to the vertical axis, along with one or more openings that allows gas to pass through. In some aspects, the shelf or roof is positioned at a transition between portions of a liquid impinger having different cross-sectional areas. In some aspects, the shelf or roof divides the liquid impinger into one or more segments, in which the two segments have the same or different cross-sectional areas. In some aspects, a shelf or roof is present at the transition point between the expanded portion and a substantially straight-walled portion.

In some aspects, the liquid impinger comprises, in sequential order, a bottom portion comprising a cylindrical wall extending substantially along at least a portion of the vertical axis, an expanded portion (e.g., substantially spherical or ellipsoidal), a substantially straight-walled portion, and a tapered portion. In some aspects, the liquid impinger comprises, in sequential order, a bottom portion comprising a cylindrical wall extending substantially along at least a portion of the vertical axis, an expanded portion (e.g., substantially spherical or ellipsoidal), and a tapered portion. In some aspects, the liquid impinger comprises, in sequential order, a bottom portion comprising a substantially spherical or ellipsoidal shape, an expanded portion (e.g., substantially spherical or ellipsoidal), a substantially straight-walled portion, and a tapered portion. In some aspects, the liquid impinger comprises, in sequential order, a bottom portion comprising a substantially spherical or ellipsoidal shape, an expanded portion (e.g., substantially spherical or ellipsoidal), and a tapered portion.

In some aspects, the liquid impinger is configured to operate with any suitable volume of the liquid. In some aspects, the liquid impinger is configured to operate with a volume (mL) of the liquid of 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200. Each of the foregoing numbers can be preceded by the word "about," "at least," "at least about," "less than," or "less than about," and any of the foregoing numbers can be used singly to describe a single point or an open-ended range, or can be used in combination to describe multiple single points or a close-ended range. For example, in some aspects, the volume (mL) is 30 to 200, less than 150, 20 to 100, 20 to 150, 25 to 120, or 15 to 200.

In some aspects, the liquid impinger contains a suitable volume of the liquid. In some aspects, the volume (mL) of the liquid is 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200. Each of the foregoing numbers can be preceded by the word "about," "at least," "at least about," "less than," or "less than about," and any of the foregoing numbers can be used singly to describe a single point or an open-ended range, or can be used in combination to describe multiple single points or a close-ended range. For example, in some aspects, the volume (mL) is 30 to 200, less than 110, 60 to 80, 20 to 150, 25 to 120, 15 to 200, 30 to 100, or less than 180.

In some aspects, the liquid impinger is filled with liquid to any suitable level. For example, in some aspects, the liquid fills at least a portion of the bottom portion. In some aspects, the liquid fills the bottom portion to within 1 cm of the top of the bottom portion (e.g., the bottom of the expanded portion when present). In some aspects, the liquid fills the entire bottom portion. In some aspects, the liquid impinger comprises, in sequential order, a bottom portion comprising a cylindrical wall extending substantially along at least a portion of the vertical axis, and an expanded portion, and the liquid impinger comprises the liquid filling the entire bottom portion, but not filling any portion of the expanded portion (in some aspects, the liquid fills the entire bottom portion and at least a portion of the expanded portion).

In some aspects, the liquid impinger has any suitable height, i.e., the length along the vertical axis and excluding any hoses or other attachments to the liquid impinger. In some aspects, the height (cm) is 5, 6, 7, 8, 9, 10, 11, 12, 13, 14, 15, 16, 17, 18, 19, 20, 21, 22, 23, 24, 25, 26, 27, 28, 29, 30, 32, 34, 36, 38, 40, 42, 44, 46, 48, or 50. Each of the foregoing numbers can be preceded by the word "about," "at least," "at least about," "less than," or "less than about," and any of the foregoing numbers can be used singly to describe a single point or an open-ended range, or can be used in combination to describe multiple single points or a close-ended range. For example, in some aspects, the height (cm) is 5 to 20, 10 to 20, less than 30, 15 to 18, or 25 to 44.

In some aspects, the liquid impinger has any suitable width, i.e., the dimension perpendicular to the vertical axis, excluding any hoses or other attachments to the liquid impinger. In some aspect, the width (cm) is 3, 4, 5, 6, 7, 8, 9, 10, 11, 12, 13, 14, or 15. Each of the foregoing numbers can be preceded by the word "about," "at least," "at least about," "less than," or "less than about," and any of the foregoing numbers can be used singly to describe a single point or an open-ended range, or can be used in combination to describe multiple single points or a close-ended range. For example, in some aspects, the width (cm) is 3 to 8, less than 10, or 5 to 15. As used herein, the width can refer to the width at the widest point of the liquid impinger (which can be, e.g., the bottom portion, expanded portion, straight-walled portion, gas outlet, or gas inlet), the width of the liquid impinger at the expanded portion (if present) or the bottom portion, or the width at the gas outlet, as will be clear from context.

In some aspects, at least a portion of the liquid impinger is composed of a material sufficiently transparent to radiation to enable sterilization of the liquid, if present, and the interior via irradiation. In some aspects, the material is the polymeric material described elsewhere herein. In some aspects, the material is different than the polymeric material. In some aspects, the radiation comprises beta, gamma, X-ray, e-beam, or any combination thereof. In some aspects, the radiation comprises beta radiation, gamma radiation, or a combination thereof. In some aspects, the radiation comprises ionizing radiation. In some aspects, the radiation comprises shortwave radiation. In some aspects, the radiation comprises high intensity radiation. In some aspects, the radiation comprises ionizing, shortwave, high intensity radiation comprising beta radiation, gamma radiation, or a combination thereof.

In some aspects, the liquid impinger is configured to be disposable. In some aspects, the liquid impinger is configured to be used once for monitoring a gas flow and then discarded. In some aspects, the liquid impinger is configured to be disposable by way of being constructed of a polymeric material and not being constructed of glass.

In some aspects, the liquid impinger comprises a port for testing the liquid impinger. In some aspects, the liquid impinger does not comprise a port for testing the liquid impinger.

In some aspects, disclosed is a method comprising:
providing a liquid impinger, the liquid impinger comprising:
a vessel comprising a vertical axis, a top portion, an interior containing a liquid, and a bottom portion comprising an interior base,
a gas inlet in fluid communication with the interior via at least one nozzle positioned in the interior and attached to the bottom portion, wherein the nozzle comprises a nozzle opening and the nozzle opening is submerged in the liquid, and
a gas outlet in fluid communication with the interior, wherein the gas inlet, the at least one nozzle, the interior, and the gas outlet sequentially define a gas flow path, transporting a gas comprising analytes along the gas flow path and through the liquid, and transferring from the gas into the liquid at least a portion of the particles; optionally wherein the analytes comprise particles, molecular analytes or a combination thereof, and further optionally for some embodiments wherein the analytes comprise biological particles.

In some aspects, the liquid impinger employed in the methods is the same liquid impinger described elsewhere herein. As a result, the disclosures set forth elsewhere herein pertaining to the liquid impinger are equally applicable here with respect to the liquid impinger employed in the methods.

In some aspects, the gas comprising particles, molecular analytes or both comprises any suitable components. In some aspects, the gas comprises, consists of, or consists essentially of a sample gas. In some aspects, the sample gas typically comprises particles, but in in some aspects the sample gas is free of, or substantially free of, particles (e.g., undetectable using standard cleanroom particle detection techniques), particularly when the sample gas is derived from a cleanroom environment that is operating under ideal, uncontaminated conditions such that the atmosphere of the cleanroom environment is free of or substantially free of particles. In some aspects, the sample gas comprises a carrier gas or sample medium, for example, air, process gases, nitrogen, argon, carbon dioxide, carbon monoxide, oxygen, or any combination thereof. In some aspects, the sample gas comprises the air present in the environment to be sampled, such as the air inside a cleanroom, an isolator, a restrictive access barrier system (RABS), or a manufacturing facility (e.g., a semiconductor or pharmaceutical manufacturing facility). In some aspects, the sample gas consists of the air (and any particles contained therein) from the environment to be sampled. In some aspects, the air in the environment is mixed with a carrier gas, such as additional air, process gases, nitrogen, argon, carbon dioxide, carbon monoxide, oxygen, or any combination thereof, prior to or during the transferring step of the method, and in such cases the sample gas comprises the air from the environment to be sampled in combination with the carrier gas. In some aspects, the sample gas not does contain a carrier gas, and such sample gas consists of the air (and any entrained particles) present in the environment to be sampled.

In some aspects, the liquid impinger comprises at least two components, and the method further comprises, prior to the providing step, filling the vessel with the liquid prior to or after assembly of the at least two components. In some aspects, the liquid impinger comprises at least two components, and the method further comprises, after the providing step, filling the vessel with the liquid prior to or after assembly of the at least two components. In some aspects, the liquid impinger is assembled from at least two components, and then the liquid impinger is filled with the liquid. In some aspects, the liquid impinger, prior to assembly of the at least two components, is filled with liquid, and then the liquid impinger is assembled from the at least two components. The assembly can be performed as described elsewhere herein. In some aspects, assembly and filling, in any order, is performed prior to providing the liquid impinger to the end user. In some aspects, assembly is performed prior to providing the liquid impinger to the end user, and the end user fills the vessel with the liquid. In some aspects, the end user assembles and fills the liquid impinger.

In some aspects, the method further comprises, prior to the transporting step, irradiating the liquid impinger in assembled form and/or filled form with radiation to sterilize at least a portion of the interior and at least a portion of the liquid contained therein, wherein at least a portion of the liquid impinger is composed of a material sufficiently transparent to the radiation to enable the sterilization. In some aspects, the entirety of the liquid contained therein is sterilized. In some aspects, the entirety of the interior is sterilized. In some aspects, the entire liquid impinger is composed of such transparent material. In some aspects, at least a portion of the bottom of the liquid impinger containing the liquid is composed of such material, for example, the side walls of the bottom portion are composed of such material. In some aspects, the entire bottom portion of the liquid impinger is composed of such material, for example, including the interior base. In some aspects, the bottom portion of the liquid impinger contains at least one window of such material, for example, in the side wall. In some aspects, the bottom portion is not transparent to such radiation; for example, in some aspects the expanded portion is sufficiently transparent to radiation to enable sterilization of at least a portion of the interior and at least a portion of the liquid contained therein.

In some aspects, at least a portion of the analytes comprise particles, molecular analytes, or a combination thereof. In some aspects, at least a portion of the analytes comprises biological particles, optionally viable biological particles. For example, in some aspects, at least a portion of the analytes comprises viruses, spores, microorganisms, bacteria, fungi, archaea, protists, single-cell microorganisms, or any combination thereof.

In some aspects, the method further comprises, after the transferring, placing caps, stoppers, or other obstructions on the gas inlet and gas outlet to prevent exposing the liquid to particles or other contaminants prior to or during the incubation and/or detecting steps. For example, after a gas has been sampled from a cleanroom environment, caps are placed on the gas inlet and outlet to prevent collection of contaminants outside of the sampling period (e.g., while transporting the impinger to a location for incubation and/or detection).

In some aspects, the transferring step is performed for any suitable time period. For example, in some aspects, the transferring step is performed for a time period (min) of 10, 20, 30, 35, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500. Each of the foregoing numbers can be preceded by the word "about," "at least," "at least about," "less than," or "less than about," and any of the foregoing numbers can be used singly to describe a single point or an open-ended range, or can be used in combination to describe multiple single points or a close-ended range. For example, in some aspects, the time period (min) is 10 to 500, 10 to 200, 20 to 80, at least 10, at least 35, 30 to 90, less than 115, or 60 to 90.

In some aspects, the method further comprises, after the transferring step, incubating the liquid under conditions sufficient to facilitate growth of viable biological particles, wherein the liquid comprises a growth medium. Suitable growth media are described elsewhere herein. In some aspects, the conditions sufficient to facilitate growth of viable biological particles comprise raising the temperature of the growth medium to above room temperature, for example, to a temperature (° C.) of 25, 26, 28, 30, 32, 34, 36, 37, 38, 40, 42, 44, or 45. Each of the foregoing numbers can be preceded by the word "about," "at least," "at least about," "less than," or "less than about," and any of the foregoing numbers can be used singly to describe a single point or an open-ended range, or can be used in combination to describe multiple single points or a close-ended range. For example, in some aspects, the temperature (° C.) for incubation is at least 25, 26 to 38, 30 to 42, or at least 30.

In some aspects, the incubation is performed for any suitable time period. For example, in some aspects, the incubation time period (min) is 1, 2, 3, 4, 5, 6, 7, 8, 9, 10, 12, 14, 16, 18, 20, 22, 24, 26, 28, 30, 40, 50, 60, 70, 80, 90, 100, 120, 140, 160, 180, 200, 250, 300, 350, 400, 450, or 500, or the time period (hour) is 1, 1.5, 2, 2.5, 3, 3.5, 4, 5, 6, 7, 8, 9, 10, 11, 12, 14, 16, 18, 20, 22, 24, 30, 36, 42, 48, 50, 55, 60, 65, 70, 72, 75, 80, 85, 90, 95, 100, 105, 110, 115, or 120. Each of the foregoing numbers can be preceded by the word "about," "at least," "at least about," "less than," or "less than about," and any of the foregoing numbers can be used singly to describe a single point or an open-ended range, or can be used in combination to describe multiple single points or a close-ended range. For example, in some aspects, the incubation time period is 2 min to 120 hours, 2 min to 30 min, 30 min to 12 hours, at least 4 hours, less than 48 hours, 24 hours to 120 hours, 36 hours to 100 hours, or 24 hours to 48 hours. In some aspects, the incubation time period generally depends on the technique used for analysis.

In some aspects, the method further comprises detecting whether contaminants, such as viable biological particles, are present in the liquid. In some aspects, the detecting step comprises at least one of: (1) optical detection comprising at least one of visual inspection by eye, an optical detector, an imaging device, use of ultraviolet-visible, near infrared, infrared, or fluorescence spectroscopy; (2) perceiving a change in oxygen level or carbon dioxide level in the liquid; or (3) analysis of the liquid after extraction from the liquid impinger using an analytical laboratory technique optionally comprising PCR. In some aspects, the detecting step comprises optical detection. In some aspects, the detecting step comprises perceiving a change in oxygen level or carbon dioxide level, or both. For example, perceiving a change in oxygen or carbon dioxide level, or both, comprises detecting such gases dissolved in or emitted from the liquid, or by way of an indicator chemical added to the liquid (e.g., titration). In some aspects, the detecting step comprises analysis of the liquid after extraction from the liquid impinger using an analytical laboratory technique. In some aspects, such analytical laboratory technique comprises the polymerase chain reaction (PCR), nucleotide sequencing, hybridization (e.g., gene probes), restriction fragment length polymorphism (RFLP) analysis, flow cytometry, fluorescent in-situ hybridization (FISH), immunological identification (e.g., enzyme-linked immunosorbent assay (ELISA)), fatty acid profiling, metabolic profiling, or any combination thereof.

In some aspects, at least one of the incubating step or the detecting step is performed without removing the liquid from the vessel or disassembling the liquid impinger. For example, in some aspects, after the transferring step, the liquid remains in the liquid impinger throughout the incubation and detection steps. In some aspects, the liquid remains in the liquid impinger during incubation, but the liquid is removed from the liquid impinger, or the liquid impinger is disassembled, prior to the detection step. In some aspects, the liquid is removed from the liquid impinger prior to incubation, and the incubation and detection steps are performed with the liquid outside of the liquid impinger. In such aspects with the liquid outside of the liquid impinger for incubation and/or detection, it is desirable to handle the liquid with care so as to prevent contamination of the liquid with particles or other contaminants so as to detect only those particles present in the liquid from the transferring step of the method.

In some aspects, performance of the filling step and the sterilizing step in combination minimizes human contact with the liquid and reduces false positives in the detecting step. In some aspects, not removing the liquid from the liquid impinger during the incubation and detection steps also minimizes human contact with the liquid and reduces false positives. In some aspects, therefore, minimizing human contact with the liquid and reducing false positives is achieved by, prior to the providing step, filling the vessel with the liquid prior to the transporting step, irradiating the liquid impinger in assembled form and/or filled form with radiation to sterilize at least a portion of the interior and at least a portion of the liquid contained therein, performing the transferring step, and then performing the incubating and detection steps (without removing the liquid from the vessel).

In some aspects, the liquid impinger is configured to be disposable. In some aspects, the method further comprises, after performing one cycle of the providing, transporting, transferring, incubating, and detecting steps, at least one of: (1) discarding the liquid impinger, (2) never again sterilizing the liquid impinger in preparation for a second cycle of the providing, transporting, transferring, incubating, and detecting steps, or (3) never again performing a second cycle of the providing, transporting, transferring, incubating, and detecting steps. In some aspects, the method further comprises, after performing one cycle of the providing, transporting, transferring, incubating, and detecting steps, discarding the liquid impinger. In some aspects, the method further comprises, after performing one cycle of the providing, transporting, transferring, incubating, and detecting steps, not sterilizing the liquid impinger with radiation sufficient to sterilize any liquid within the liquid impinger. In some aspects, the method further comprises, after performing one cycle of the providing, transporting, transferring, incubating, and detecting steps, not performing a second cycle of the providing, transporting, transferring, incubating, and detecting steps.

As noted elsewhere herein, in some aspects, the liquid impinger employed in the methods is the same liquid impinger described elsewhere herein. As a result, the disclosures set forth elsewhere herein pertaining to the liquid impinger are equally applicable here with respect to the liquid impinger employed in the methods. For example, in some aspects of the method, the at least one nozzle comprises at least two nozzles or at least three nozzles. In some aspects of the method, each nozzle opening has a diameter of 0.1 mm to 3.2 mm. In some aspects of the method, the at least one nozzle comprises a shape comprising an arc, and the arc is substantially within a plane that makes an angle with the vertical axis of 85 degrees to 95 degrees. In some aspects of the method, the at least one nozzle has a horizontal angle of 0 degrees to 40 degrees. In some aspects of the method, the gas inlet is connected to the at least one nozzle by a tube extending from the top portion to the bottom portion within the interior. In some aspects of the method, the bottom portion comprises a cylindrical, spherical, or ellipsoidal shape, and the liquid impinger further comprises: at least one expanded portion between the bottom portion and the top portion, wherein the expanded portion has a larger internal cross-sectional area at its widest point than an internal cross-sectional area of the bottom portion at its widest point, and at least one tapered portion between the expanded portion and the top portion, wherein the at least one tapered portion tapers to a smaller internal cross-sectional area along the vertical axis toward the top portion. In some aspects of the method, the bottom portion further comprises a side wall, and the nozzle opening is positioned within 10 mm of the side wall or is substantially flush with the side wall. In some aspects, the liquid impinger comprises a polymeric material. In some aspects, the polymeric material comprises poly(acrylonitrile-butadiene-styrene), polyethylene, polycarbonate, polyamide, polystyrene, transparent polystyrene (e.g., Polystyrol™ available from BASF), high impact polystyrene, polypropylene, polyoxymethylene, polyurethane, rubber, or any combination thereof.

In some aspects, the transporting step is performed at any suitable flow rate. For example, in some aspects, the flow rate (L/min) into the gas inlet and/or out of the gas outlet, is 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20. Each of the foregoing numbers can be preceded by the word "about," "at least," "at least about," "less than," or "less than about," and any of the foregoing numbers can be used singly to describe a single point or an open-ended range, or can be used in combination to describe multiple single points or a close-ended range. For example, in some aspects, the flow rate (L/min) into the gas inlet and/or out of the gas outlet is 1 to 20, 1 to 4, 3 to 5, at least 2, at least 3.5, less than 8, 5.5 to 18, 10 to 20, 8 to 15, or 3.5 to 9.

In some aspects, the velocity of gas flowing out of a nozzle is any suitable velocity. For example, in some aspects, the velocity (m/s) of gas flowing out of a nozzle is 10, 15, 20, 25, 30, 35, 40, 45, 50, 55, 60, 65, 70, 75, 80, 85, 90, 95, 100, 105, 110, 115, or 120. Each of the foregoing numbers can be preceded by the word "about," "at least," "at least about," "less than," or "less than about," and any of the foregoing numbers can be used singly to describe a single point or an open-ended range, or can be used in combination to describe multiple single points or a close-ended range. For example, in some aspects, the velocity (m/s) of gas flowing out of a nozzle is 10 to 120, 70 to 80, less than 80, less than 85, at least 40, 45 to 120, 80 to 110, or 50 to 85. In some aspects, when two or more nozzles are employed in the liquid impinger, each nozzle independently has any velocity disclosed herein. In some aspects, when two or more nozzles are employed in the liquid impinger, each nozzle has the same velocity chosen from any velocity disclosed. In some aspects, the velocity is chosen so as to maintain the viability of (e.g., not kill or render incapable of replication) the microorganisms, viruses, or other biological particles that may be present. In some aspects, the velocity is selected so as to promote swirling of the liquid within the bottom portion. For example, in some aspects, the velocity is selected so as to promote swirling of the liquid within the bottom portion, such that bubble residence time in the gas is increased (e.g., maximized) and transfer from bubble to liquid is improved.

In some aspects, disclosed is a method for producing a liquid impinger, the method comprising:

- forming at least two components of a liquid impinger,
- optionally, assembling the at least two components to produce an assembled liquid impinger, the assembled liquid impinger comprising:
- a vessel comprising a vertical axis, a top portion, an interior, and a bottom portion comprising an interior base,
- a gas inlet in fluid communication with the interior via at least one nozzle positioned in the interior and attached to the bottom portion, wherein the nozzle comprises a nozzle opening, and
- a gas outlet in fluid communication with the interior,
- wherein the gas inlet, the at least one nozzle, the interior, and the gas outlet sequentially define a gas flow path, and
- wherein the vessel is configured to contain a liquid within the interior,
- optionally, filling a portion of the interior of the assembled liquid impinger with the liquid to produce a filled liquid impinger,
- optionally, exposing the filled liquid impinger to radiation to sterilize at least a portion of the liquid present in the interior of the liquid impinger, thereby producing a filled and sterilized liquid impinger, and
- optionally, before or after the exposing step, packaging the filled liquid impinger or the filled and sterilized liquid impinger in a manner that prevents ingress of particles or contamination into the interior of the liquid impinger.

In some aspects, disclosed is a method for producing a filled and sterilized liquid impinger, the method comprising:

- forming at least two components of a liquid impinger,
- assembling the at least two components to produce an assembled liquid impinger, the assembled liquid impinger comprising:
- a vessel comprising a vertical axis, a top portion, an interior, and a bottom portion comprising an interior base,
- a gas inlet in fluid communication with the interior via at least one nozzle positioned in the interior and attached to the bottom portion, wherein the nozzle comprises a nozzle opening, and
- a gas outlet in fluid communication with the interior,
- wherein the gas inlet, the at least one nozzle, the interior, and the gas outlet sequentially define a gas flow path, and
- wherein the vessel is configured to contain a liquid within the interior,
- filling a portion of the interior of the assembled liquid impinger with the liquid to produce a filled liquid impinger,
- exposing the filled liquid impinger to radiation to sterilize at least a portion of the liquid present in the interior of the liquid impinger, thereby producing the filled and sterilized liquid impinger, and
- optionally, before or after the exposing step, packaging the filled liquid impinger or the filled and sterilized liquid impinger in a manner that prevents ingress of particles or contamination into the interior of the liquid impinger.

In some aspects, disclosed is a method for producing a filled and sterilized liquid impinger, the method comprising:

- a first providing step, comprising providing a filled liquid impinger, wherein the filled liquid impinger comprises:
- a vessel comprising a vertical axis, a top portion, an interior, and a bottom portion comprising an interior base,
- a gas inlet in fluid communication with the interior via at least one nozzle positioned in the interior and attached to the bottom portion, wherein the nozzle comprises a nozzle opening, and
- a gas outlet in fluid communication with the interior, wherein the gas inlet, the at least one nozzle, the interior, and the gas outlet sequentially define a gas flow path, and wherein the vessel is contains a liquid within the interior, exposing the filled liquid impinger to radiation to sterilize at least a portion of the liquid present in the interior of the liquid impinger, thereby producing the filled and sterilized liquid impinger, and optionally, before or after the exposing step, packaging the filled liquid impinger or the filled and sterilized liquid impinger in a manner that prevents ingress of particles or contamination into the interior of the liquid impinger.

In some aspects, the liquid impinger employed in the methods for producing a liquid impinger, or a filled and sterilized liquid impinger, is the same liquid impinger described elsewhere herein. As a result, the disclosures set forth elsewhere herein pertaining to the liquid impinger are equally applicable here with respect to the liquid impinger employed in such methods. In addition, various aspects of the method steps describing elsewhere herein for use of the liquid impinger are applicable to the methods for producing a liquid impinger or a filled and sterilized liquid impinger. For example, the steps of filling, irradiating/sterilizing/exposing, and placing caps/stoppers are equally applicable here, though any method or method step described elsewhere herein is applicable here for the method of making.

In some aspects, any method step is performed or is not performed, including any step specified to be optional or not specified to be optional. For example, in some aspects, the assembling step is performed. In some aspects, the filling step is performed. In some aspects, the exposing step is performed. In some aspects, the packaging step is performed. In some aspects, any combination of these steps is performed. For example, in some aspects, the forming and assembling steps are performed. In some aspects, the forming, assembling and filling are performed. In some aspects, the filling and exposing steps are performed. In some aspects, the assembling, filling, and exposing steps are performed. In some aspects, the forming, assembling, filling, and exposing steps are performed. In some aspects, the forming step is optional. In some aspects, the forming step is not performed, and the assembling step is performed. In some aspects, the forming step is not performed, and the assembling and filling steps are performed. In some aspects, the forming step is not performed, and the assembling, filling, and exposing steps are performed. In some aspects, the forming step is not performed, and the filling and exposing steps are performed.

Figure 12:
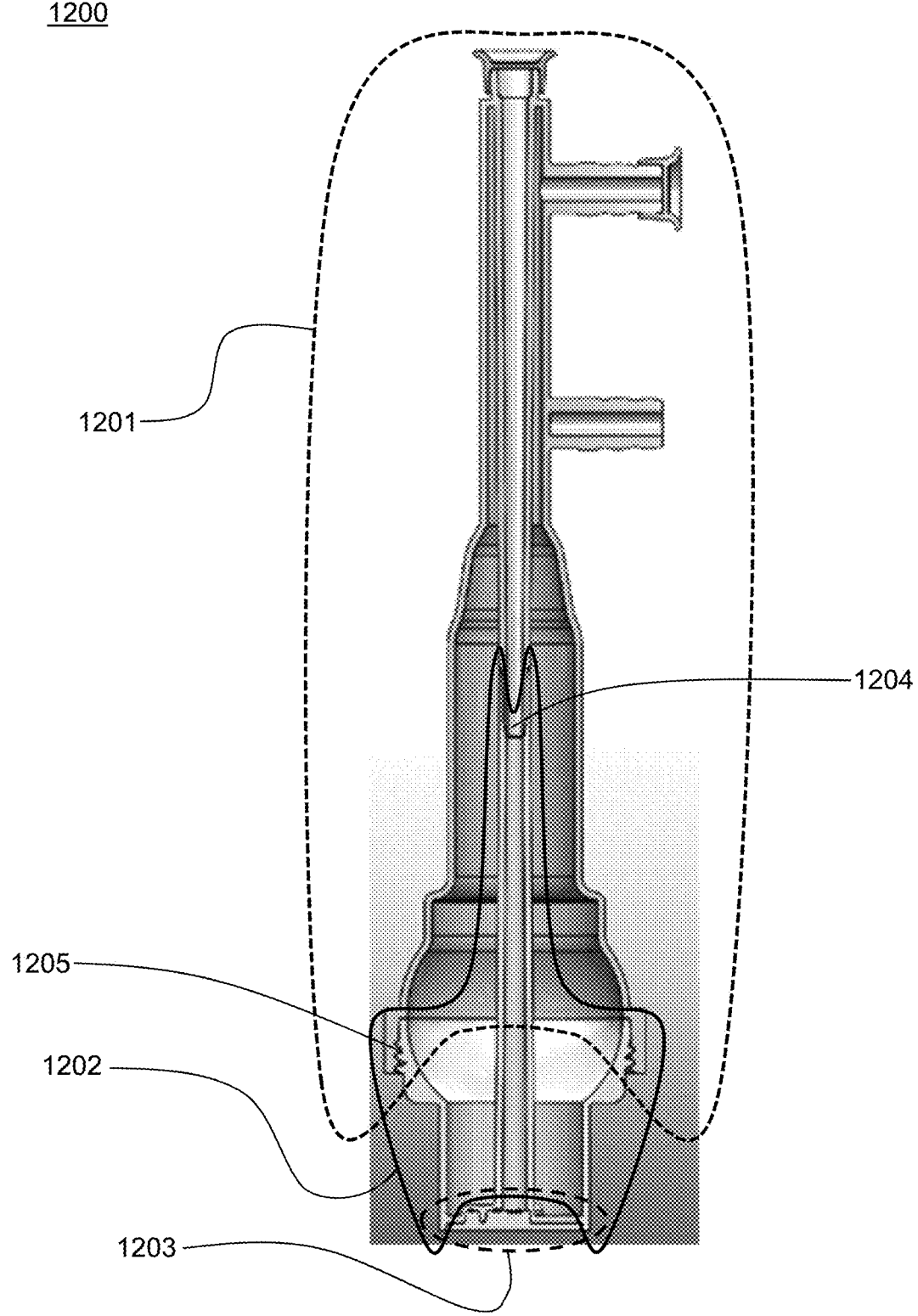
FIG. 12 depicts a three component liquid impinger with outlining indicating each separate component.

In some aspects, the assembling step is performed by attaching or connecting the various components of the liquid impinger in any suitable manner. Reference to FIG. 12 is useful for understanding an aspect of the assembling step, which figure depicts a three component liquid impinger comprising components 1201, 1202, and 1203 indicated in outlining. For example, in some aspects, component 1201 is attached to component 1202 via two attachment points: by way of abutting or wedging the smaller diameter tube of component 1201 into the larger diameter tube of component 1202 at position 1204, and by way of screwing component 1201 and 1202 together at position 1205. In some aspects, component 1202 has a smaller diameter tube that is abutted or wedged into a larger diameter tube of component 1201. In some aspects, such a connection at position 1204 and position 1205 independently can be held together in any suitable manner, for example, by friction, glue, heat melting, screwing, or any combination thereof. In FIG. 12, component 1203 is attached to component 1202, which components can be held together in any suitable manner, for example, by friction, glue, heat melting, screwing, or any combination thereof.

In some aspects, the filling step can be performed in any suitable manner. For example, in some aspects, the filing step is performed by adding liquid to the interior of the liquid impinger through the top portion, e.g., by way of the outlet. In some aspects, the filling step is performed on a liquid impinger in which the component containing the bottom portion (e.g., component 1202 in FIG. 12) is disconnected from the component containing the top portion (e.g., component 1201 in FIG. 12). In such an aspect, the filling step comprises filling the bottom portion with liquid to the desired level, and then assembling the components containing the top and bottom portions (e.g., by way of screwing). In some aspects, the filling is performed with a pipette.

In some aspects, the method further comprises, prior to the first providing step:
a second providing step, comprising providing an assembled liquid impinger, wherein the assembled liquid impinger comprises the filled liquid impinger without the liquid, and
filling a portion of the interior of the assembled liquid impinger with the liquid to produce the filled liquid impinger.

In some aspects, the assembled liquid impinger is fully assembled or partially assembled, and the filling step is performed on the fully assembled or partially assembled liquid impinger. In some aspects, the fully assembled or partially assembled liquid impinger is configured to contain a liquid within the interior. In some aspects, when the assembled liquid impinger is a partially assembled liquid impinger, the filling step is performed, and then the partially assembled liquid impinger is fully assembled. In some aspects, when the assembled liquid impinger is a partially assembled liquid impinger, the filling step is performed, then the partially assembled liquid impinger is fully assembled, and then the exposing step is performed on the fully assembled liquid impinger. In some aspects, when the assembled liquid impinger is a partially assembled liquid impinger, the filling step is performed, then the exposing step is performed on the filled partially assembled liquid impinger, and then the partially assembled liquid impinger is fully assembled.

In some aspects, the method further comprises prior to the second providing step: assembling at least two components to produce the assembled liquid impinger. In some aspects, the at least two components comprises three components, four components, five components, six components, or seven components.

In some aspects, the method further comprises, prior to the assembling step: forming the at least two components. In some aspects, the forming step comprises molding, injection molding, blow molding, rotational molding, additive manufacturing, three-dimensional printing, subtractive manufacturing, casting, forming, vacuum forming, extrusion, or any combination thereof.

In some aspects, the forming step forms one or more polymeric materials into the at least two components. In some aspects, the one or more polymeric materials comprise poly(acrylonitrile-butadiene-styrene), polyethylene, polycarbonate, polyamide, polystyrene, transparent polystyrene (e.g., Polystyrol™ available from BASF), high impact polystyrene, polypropylene, polyoxymethylene, polyurethane, rubber, or any combination thereof. Other suitable polymeric materials are described elsewhere herein.

In some aspects, the radiation comprises beta, gamma radiation, X-ray radiation, e-beam radiation, or any combination thereof.

In some aspects, the liquid comprises a growth medium.

In some aspects, the methods further comprise, prior to the filling step, irradiating the at least two components, the assembled liquid impinger, or both, with radiation for sterilization, the radiation comprising beta, gamma radiation, X-ray radiation, e-beam radiation, or any combination thereof. Such radiation can be the same or different as the exposing step. In some aspects, the methods can use of radiation prior to, during, or after any step so as to sterilize at least a portion of the interior, any components that will form at least part of the interior, or any liquid contained in the interior, or any combination thereof.

In some aspects, before or after the exposing step, the filled liquid impinger or the filled and sterilized liquid impinger is packaged in a manner that prevents ingress of particles or contamination into the interior of the liquid impinger. In some aspects, the packaging step is performed before the exposing step. In some aspects, the packaging step is performed after the exposing step. In some aspects, the packaging step is performed and comprises (1) attaching caps to one or more gas inlets and outlets, (2) sealing the filled liquid impinger or the filled and sterilized liquid impinger into a container, or (3) a combination thereof. In some aspects, the container is a bag, for example, a plastic bag. In some aspects, the container (e.g., a bag) is impermeable or semi-permeable to particles having a size in a range that the method of using the liquid impinger is configured to detect, such that the container effectively prevents ingress of such particles or contamination into the liquid impinger to avoid false positives. In some aspects, the packaging step comprises enclosing the liquid impinger in one layer of packaging (e.g., a container or bag). In some aspects, the packaging step comprises enclosing the liquid impinger in at least two layers of packaging, for example, to enable proper handling when entering a clean room or other sterile zone. Any suitable packaging material may be used. For example, in some aspects, plastics such as polypropylene or polyethylene may be used as the packaging material.

Aspects of the invention can be further understood by the following non-limiting figures.

FIG. 1. depicts some aspects of a liquid impinger, in particular, a liquid impinger for sampling a gas. Liquid impinger 100 comprises a vertical axis 101, a top portion 102, a bottom portion 103, a gas inlet 104, a gas outlet 105, an interior 106, an interior base 107, a nozzle 108, a nozzle opening 109, a tube 110, and side wall 113. The bottom portion 103 comprises interior base 107. The gas inlet 104 is in fluid communication with interior 106 via nozzle 108 positioned in the interior 106 and attached to the bottom portion 103. Although nozzle 108 is depicted as attached to interior base 107, nozzle 108 can be attached or located anywhere within the bottom portion 103, e.g., nozzle 108 can be attached to side wall 113. The gas inlet 104 is connected to the nozzle 108 by tube 110 extending from the top portion 102 to the bottom portion 103 within the interior 106. Gas outlet 105 is in fluid communication with interior 106. A gas flow path is sequentially defined by gas inlet 104, nozzle 108, interior 106, and gas outlet 105. The gas flow path bends at an angle of 80 degrees to 100 degrees between the tube 110 and the nozzle 108. Bottom portion 103 comprises a wall extending substantially along at least a portion of the vertical axis 101, and such wall can be cylindrical. Gas outlet 105 is located in the top portion 102. Liquid impinger 100 does not comprise an expanded portion, nor a tapered portion, nor liquid.

Figure 2:
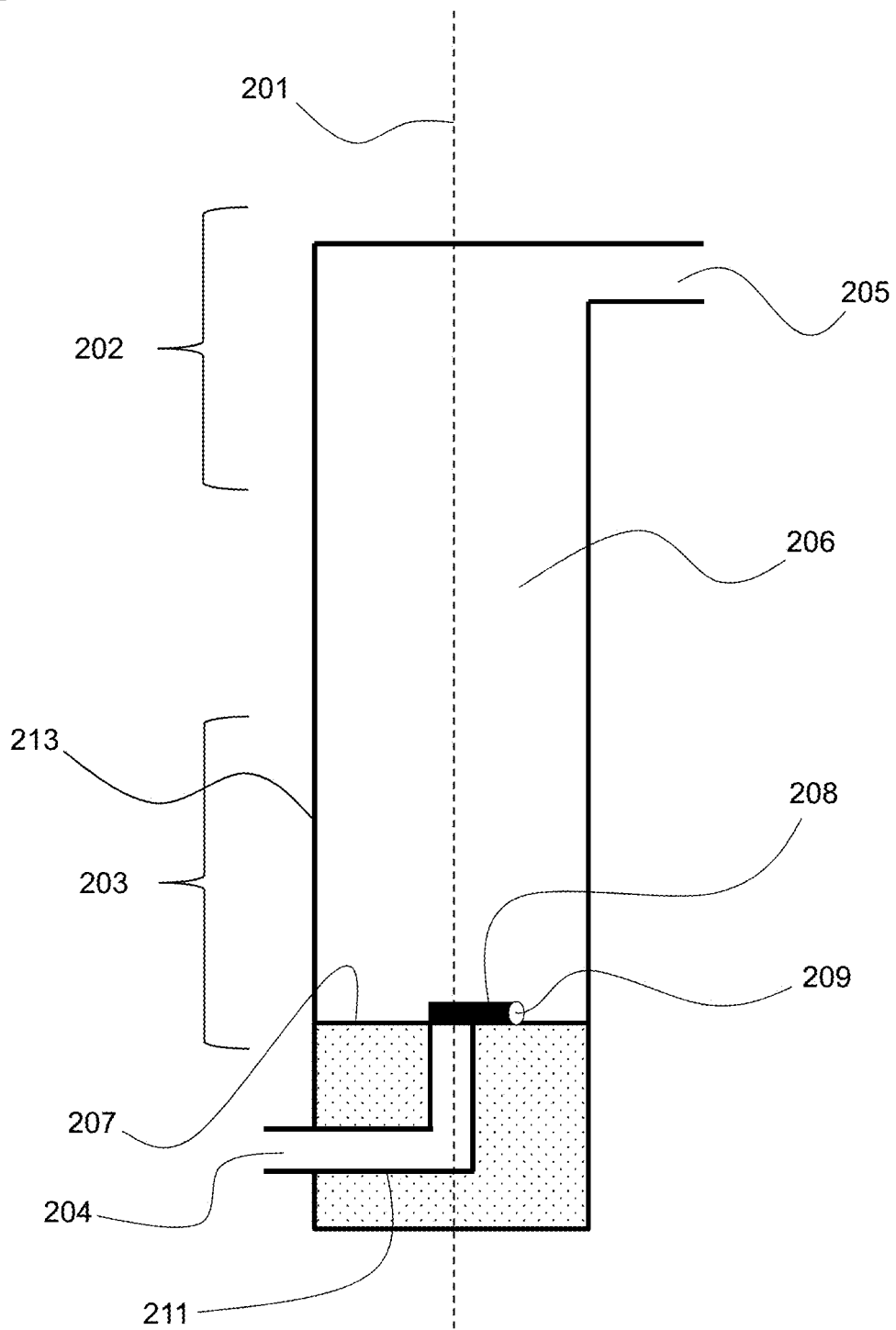
FIG. 2. depicts some aspects of a liquid impinger similar to FIG. 1, except that the tube supplying the gas approaches from the bottom of the liquid impinger, rather than a tube extending through the interior.

FIG. 2. depicts some aspects of a liquid impinger, in particular, a liquid impinger for sampling a gas. Liquid impinger 200 of FIG. 2 is similar to liquid impinger 100 of FIG. 1, except the tube supplying the gas approaches from the bottom of the liquid impinger, rather than a tube extending through the interior. Liquid impinger 200 comprises a vertical axis 201, a top portion 202, a bottom portion 203, a gas inlet 204, a gas outlet 205, an interior 206, an interior base 207, a nozzle 208, a nozzle opening 209, a tube 211, and side wall 213. The bottom portion 203 comprises interior base 207. The gas inlet 204 is in fluid communication with interior 206 via nozzle 208 positioned in the interior 206 and attached to the bottom portion 203. Although nozzle 208 is depicted as attached to interior base 207, nozzle 208 can be attached or located anywhere within the bottom portion 203, e.g., nozzle 208 can be attached to side wall 213. The gas inlet 204 is connected to the nozzle 208 by tube 211 approaching the bottom portion 103 from below liquid impinger 200. Gas outlet 205 is in fluid communication with interior 206. A gas flow path is sequentially defined by gas inlet 204, nozzle 208, interior 206, and gas outlet 205. The gas flow path bends at an angle of 80 degrees to 100 degrees between the tube 210 and the nozzle 208. Bottom portion 203 comprises a wall extending substantially along at least a portion of the vertical axis 201, and such wall can be cylindrical. Gas outlet 205 is located in the top portion 202. Liquid impinger 200 does not comprise an expanded portion, nor a tapered portion, nor liquid.

Figure 3:
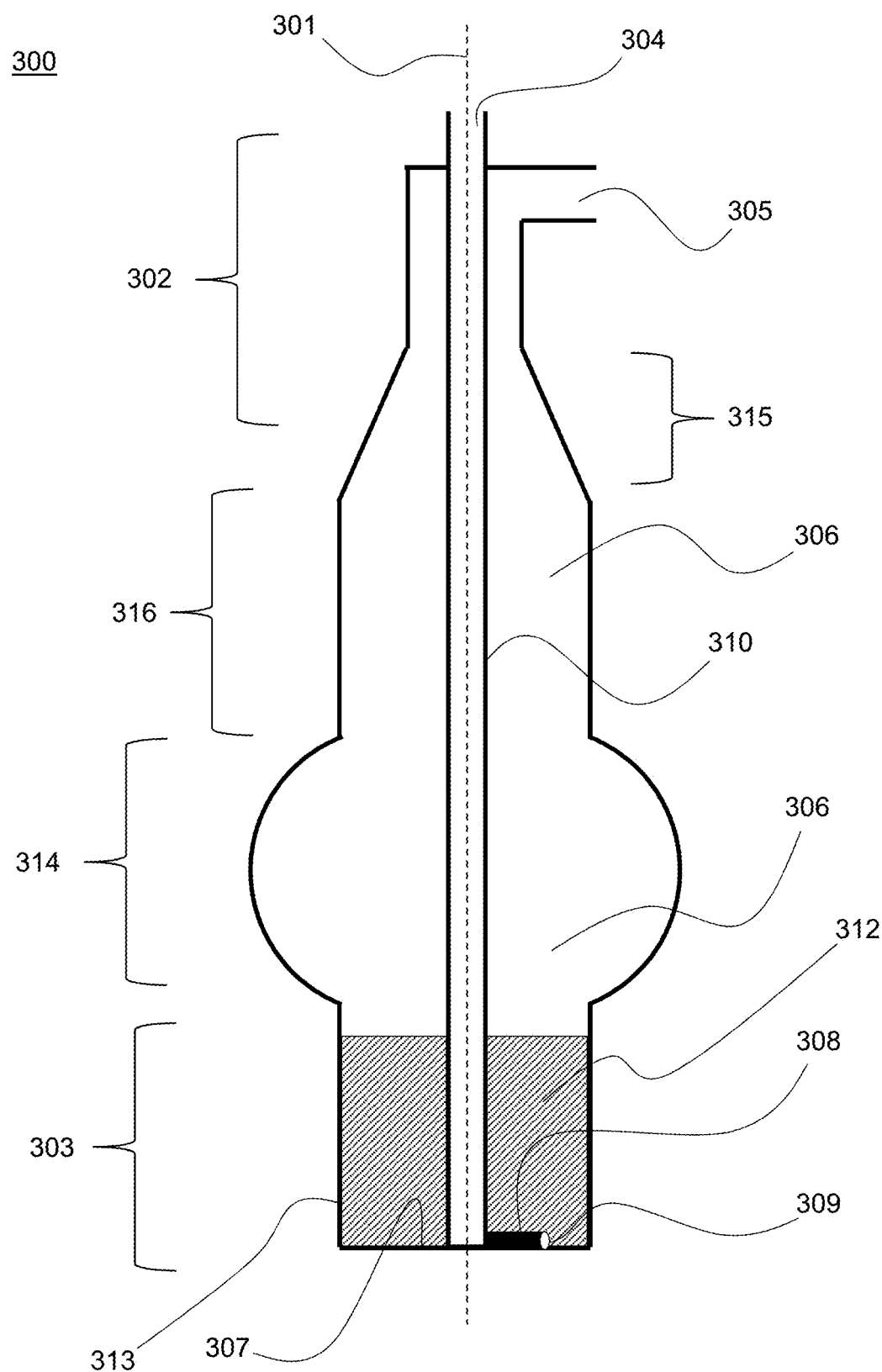
FIG. 3. depicts some aspects of a liquid impinger similar to FIG. 1, except that the liquid impinger additionally comprises, for example, liquid, an expanded portion, and a tapered portion.

FIG. 3. depicts some aspects of a liquid impinger, in particular, a liquid impinger for sampling a gas. Liquid impinger 300 of FIG. 3 is similar to liquid impinger 100 of FIG. 1, except liquid impinger 300 additionally comprises, for example, liquid, an expanded portion, and a tapered portion. Liquid impinger 300 comprises a vertical axis 301, a top portion 302, a bottom portion 303, a gas inlet 304, a gas outlet 305, an interior 306, an interior base 307, a nozzle 308, a nozzle opening 309, a tube 310, liquid 312, side wall 313, expanded portion 314, tapered portion 315, and substantially straight-walled portion 316. The bottom portion 303 comprises interior base 307. The gas inlet 304 is in fluid communication with interior 306 via nozzle 308 positioned in the interior 306 and attached to the bottom portion 303. Although nozzle 308 is depicted as attached to interior base 307, nozzle 308 can be attached or located anywhere within the bottom portion 303, e.g., nozzle 308 can be attached to side wall 313. The gas inlet 304 is connected to the nozzle 308 by tube 310 extending from the top portion 302 to the bottom portion 303 within the interior 306. Gas outlet 305 is in fluid communication with interior 306. A gas flow path is sequentially defined by gas inlet 304, nozzle 308, interior 306, and gas outlet 305. The gas flow path bends at an angle of 80 degrees to 100 degrees between the tube 310 and the nozzle 308. Nozzle 308 is submerged in the liquid 312, and transporting a gas along the gas flow path causes the gas to pass through the liquid 312. The liquid 312 fills the bottom portion nearly to the point where the bottom portion connects to the expanded portion (though in some aspects, the liquid can fill the entire bottom portion and in some aspects a portion of the expanded portion, or the liquid can fill even less of the bottom portion). Bottom portion 303 comprises a wall extending substantially along at least a portion of the vertical axis 301, and such wall can be cylindrical. The liquid impinger 300 comprises in sequential order bottom portion 303, expanded portion 314 (substantially spherical or ellipsoidal shape), substantially straight-walled portion 316, and tapered portion 315. Tapered portion 315 has a relatively quick or sharp taper. Gas outlet 305 is located in the top portion 302. During operation, gas is passed into gas inlet 304, along tube 310, through nozzle 308, out nozzle opening 309, through liquid 312, through the interior 306 by way of the expanded portion 314, substantially straight-walled portion 316, tapered portion 315, and out gas outlet 305. In some aspects, transporting gas through the liquid impinger causes the liquid 312 to swirl within the bottom portion 303.

Figure 4:
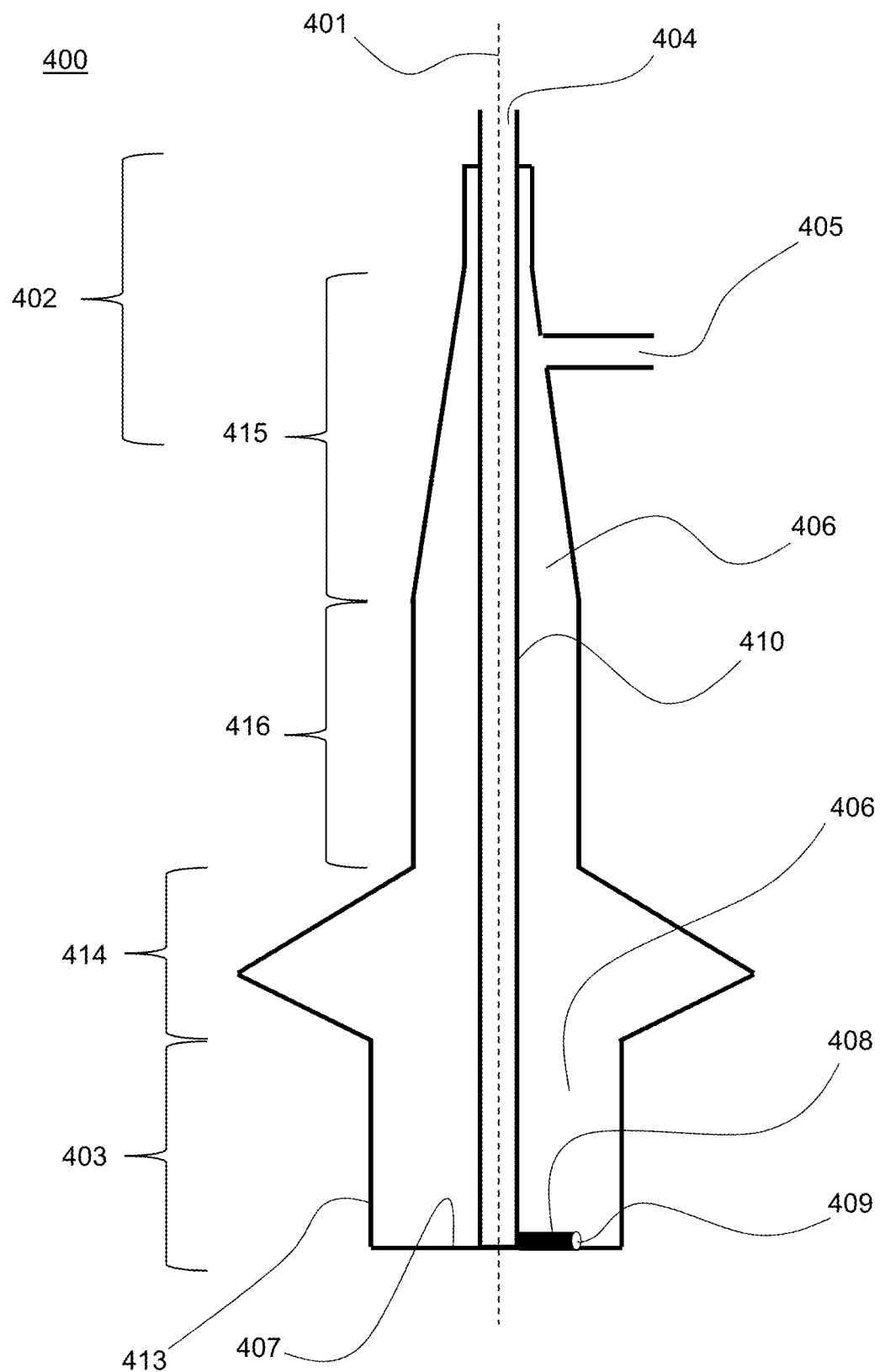
FIG. 4. depicts some aspects of a liquid impinger similar to FIG. 3, except that the liquid impinger, for example, has a differently shaped expanded portion and a tapered portion with a more gradual taper.

FIG. 4. depicts some aspects of a liquid impinger, in particular, a liquid impinger for sampling a gas. Liquid impinger 400 of FIG. 4 is similar to liquid impinger 300 of FIG. 3, except, for example, the expanded portion of liquid impinger 400 is different in some respects. Liquid impinger 400 comprises a vertical axis 401, a top portion 402, a bottom portion 403, a gas inlet 404, a gas outlet 405, an interior 406, an interior base 407, a nozzle 408, a nozzle opening 409, a tube 410, side wall 413, expanded portion 414, tapered portion 415, and substantially straight-walled portion 416. The bottom portion 403 comprises interior base 407. The gas inlet 404 is in fluid communication with interior 406 via nozzle 408 positioned in the interior 406 and attached to the bottom portion 403. Although nozzle 408 is depicted as attached to interior base 407, nozzle 408 can be attached or located anywhere within the bottom portion 403, e.g., nozzle 408 can be attached to side wall 413. The gas inlet 404 is connected to the nozzle 408 by tube 410 extending from the top portion 402 to the bottom portion 403 within the interior 406. Gas outlet 405 is in fluid communication with interior 406. A gas flow path is sequentially defined by gas inlet 404, nozzle 408, interior 406, and gas outlet 405. The gas flow path bends at an angle of 80 degrees to 100 degrees between the tube 410 and the nozzle 408. Although liquid is not depicted, nozzle 408 would be submerged in the liquid if it was present, and transporting a gas along the gas flow path would cause the gas to pass through the liquid. Bottom portion 403 comprises a wall extending substantially along at least a portion of the vertical axis 401, and such wall can be cylindrical. The liquid impinger 400 comprises in sequential order bottom portion 403, expanded portion 414 (triangular shape), substantially straight-walled portion 416, and tapered portion 415. Tapered portion 415 has a relatively gradual taper. Gas outlet 405 is located in the top portion 402. During operation, gas is passed into gas inlet 404, along tube 410, through nozzle 408, out nozzle opening 409, through liquid when present, through the interior 406 by way of the expanded portion 414, substantially straight-walled portion 416, tapered portion 415, and out gas outlet 405. In some aspects, transporting gas through the liquid impinger causes the liquid when present to swirl within the bottom portion 403.

Figure 5:
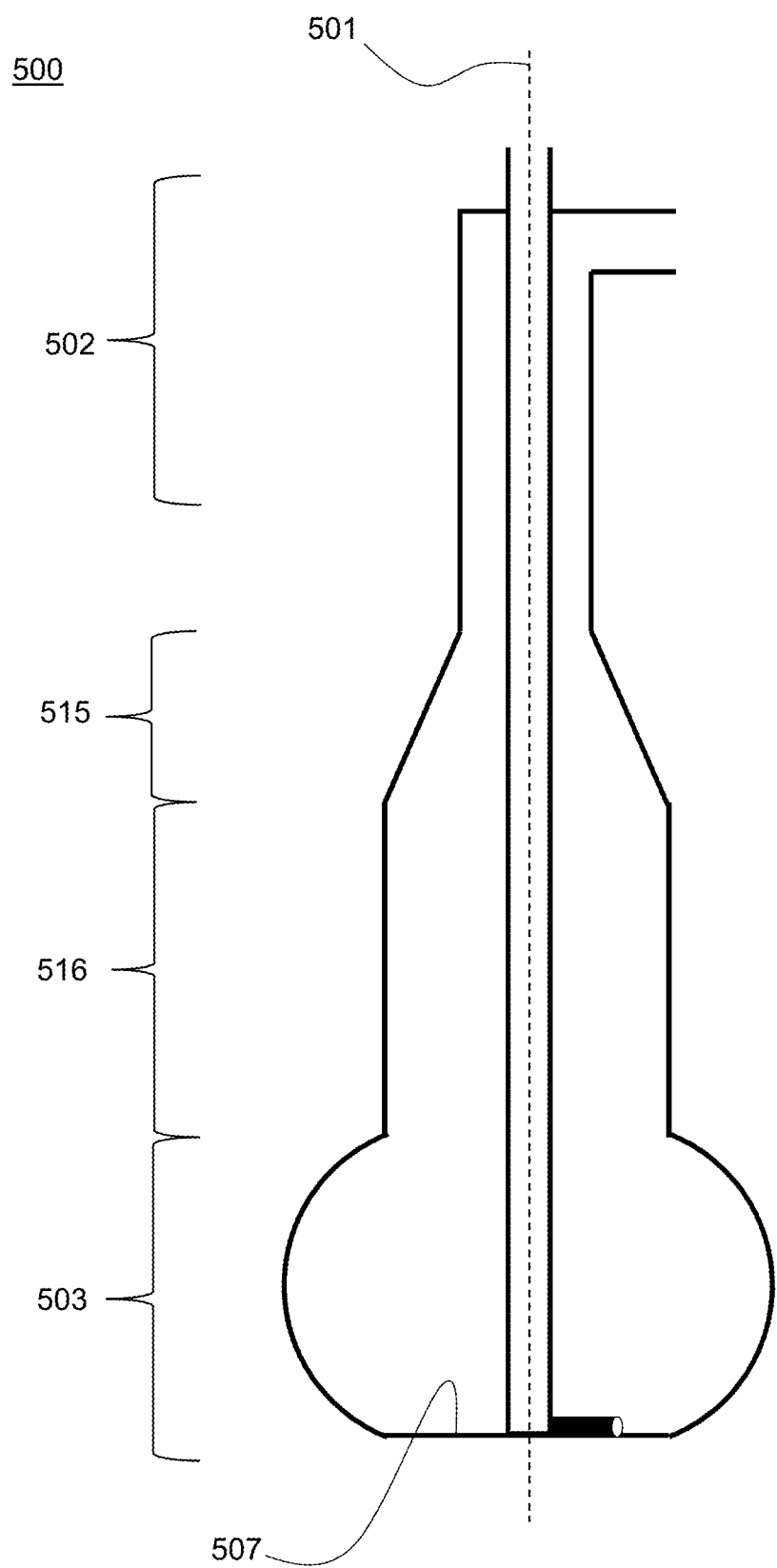
FIG. 5. depicts some aspects of a liquid impinger similar to FIG. 4, except that the liquid impinger, for example, has differently shaped bottom portion and lack of an expanded portion located above the bottom portion.

FIG. 5. depicts some aspects of a liquid impinger, in particular, a liquid impinger for sampling a gas. Liquid impinger 500 of FIG. 5 is similar to liquid impinger 300 of FIG. 3 and liquid impinger 400 of FIG. 4, except, for example, the bottom portion in liquid impinger 500 is shaped differently. All features of FIG. 5 not specifically defined are the same as in FIGS. 3 and 4. Liquid impinger 500 comprises vertical axis 501, top portion 502, tapered portion 515, substantially straight-walled portion 516, bottom portion 503, and interior base 507. Bottom portion 503 comprises a spherical or ellipsoidal shape. Although the interior base 507 is depicted as flat, any suitable shape can be employed, as described elsewhere herein, such as spherical, concave, or convex. Operation of liquid impinger 500 according to the methods disclosed herein is similar to that described for the other figures herein, such as FIGS. 3 and 4.

Figure 6A:
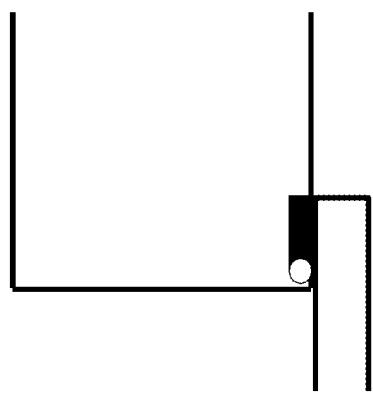
FIGS. 6A-6D. depict some aspects of a liquid impinger similar to those shown in other figures, except that, for example, the interior base has different shapes, nozzle configurations, and/or attachment geometry between the gas-supplying tube and the nozzle(s).
Figure 6B:
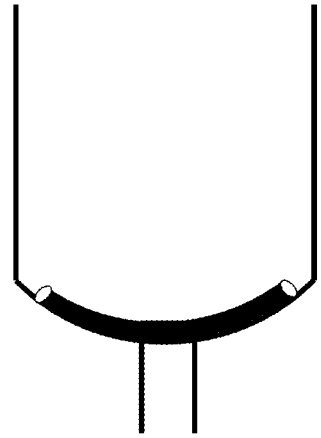
Figure 6C:
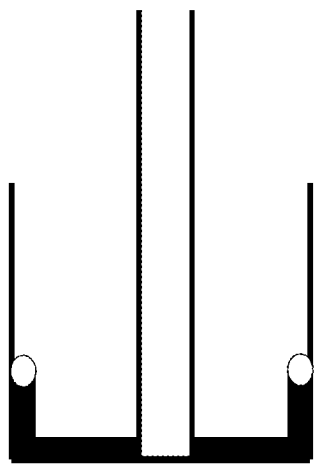
Figure 6D:
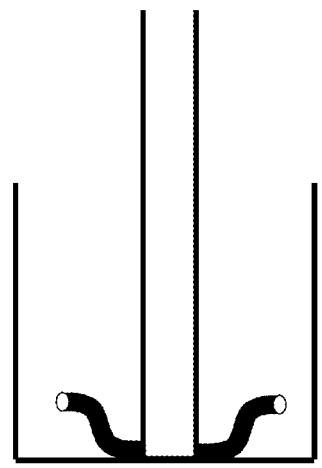

FIGS. 6A-D depicts some aspects of a liquid impinger. For example, FIGS. 6A-D depicts various nozzle configurations in the bottom portion of a liquid impinger. FIG. 6A depicts a configuration of the bottom portion of a liquid impinger in which the nozzle is supplied with gas flow via a tube attached to the side wall of the bottom portion. The nozzle direction is perpendicular to the plane of the figure sheet. FIG. 6B depicts a configuration of the bottom portion of a liquid impinger in which two nozzles are supplied with gas flow via a tube approaching the bottom portion from below, and the interior base of the bottom portion has a concave, spherical, or ellipsoidal shape. The nozzle direction is perpendicular to the plane of the figure sheet, or is angled upwards toward the side wall. FIG. 6C depicts a configuration of the bottom portion of a liquid impinger in which two nozzles are supplied with gas flow via a tube positioned in the interior of the liquid impinger, in which the nozzles are attached to the interior base and optionally the side wall. The nozzle direction is perpendicular to the plane of the figure sheet. FIG. 6D depicts a configuration of the bottom portion of a liquid impinger in which two nozzles are supplied with gas flow via a tube positioned in the interior of the liquid impinger, in which the nozzles optionally are attached to the interior base. The nozzle direction is perpendicular to the plane of the figure sheet or angled toward the side wall (but not perpendicular to the side wall).

FIG. 7A and FIG. 7B depict aspects of nozzle configurations. In particular, FIG. 7A and FIG. 7B depict the interior base 709 of the bottom portion of a liquid impinger as viewed from the direction of the top portion along the vertical axis. Three nozzles 708 are present in each figure, and each nozzle comprises nozzle opening 709 and each nozzle comprises a shape comprising an arc. The arc is substantially within a plane that makes an angle with the vertical axis of 85 degree to 95 degrees. Feature 721 identifies the location where a tube supplying gas flow from a gas inlet would be located. Other features of FIG. 7A and FIG. 7B are described elsewhere herein to aid in understanding the definition of the term "horizontal angle."

FIG. 8 is described elsewhere herein to aid in understanding the definition of the term "vertical angle."

Figure 9:
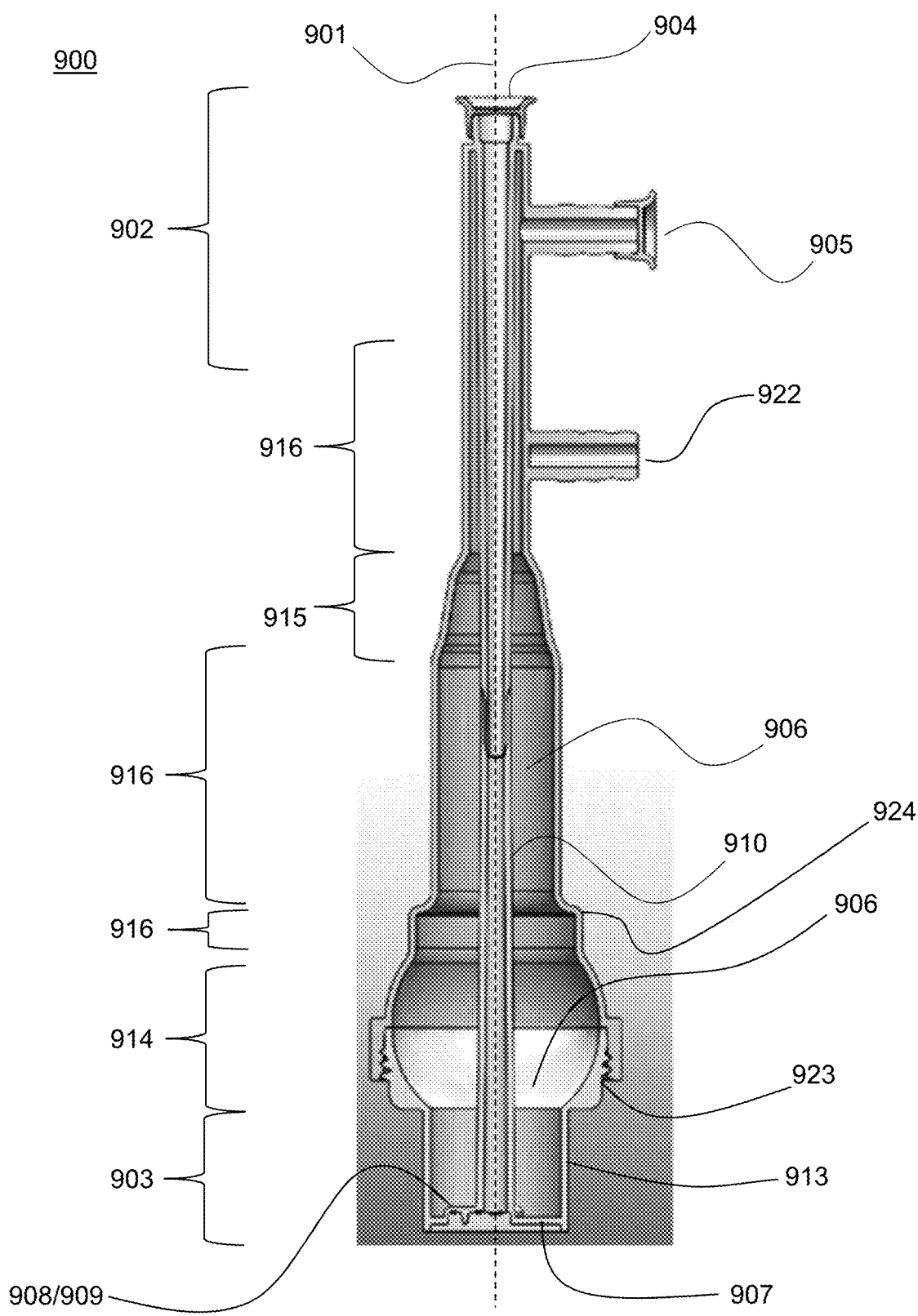
FIG. 9. depicts a detailed version of a liquid impinger similar to FIG. 3.

FIG. 9. depicts some aspects of a liquid impinger, in particular, a liquid impinger for sampling a gas. Liquid impinger 900 comprises a vertical axis 901, a top portion 902, a bottom portion 903, a gas inlet 904, a gas outlet 905, an interior 906, an interior base 907, a nozzle 908, a nozzle opening 909, a tube 910, side wall 913, expanded portion 914, tapered portion 915, and three substantially straight-walled portions 916. The bottom portion 903 comprises interior base 907. The gas inlet 904 is in fluid communication with interior 906 via nozzle 908 positioned in the interior 906 and attached to the bottom portion 903. The gas inlet 904 is connected to the nozzle 908 by tube 910 extending from the top portion 902 to the bottom portion 903 within the interior 906. Gas outlet 905 is in fluid communication with interior 906. A gas flow path is sequentially defined by gas inlet 904, nozzle 908, interior 906, and gas outlet 905. The gas flow path bends at an angle of 80 degrees to 100 degrees between the tube 910 and the nozzle 908. Although liquid is not depicted, nozzle 908 would be submerged in the liquid if it was present, and transporting a gas along the gas flow path would cause the gas to pass through the liquid. Bottom portion 903 comprises a wall extending substantially along at least a portion of the vertical axis 901, and such wall can be cylindrical. The liquid impinger 900 comprises in sequential order bottom portion 903, expanded portion 914 (substantially spherical or ellipsoidal shape), substantially straight-walled portion 916, a shelf 924 allowing transition to substantially straight-walled portion 916 with smaller cross-sectional area, tapered portion 915, and another substantially straight walled portion 916. Tapered portion 915 has a relatively quick or sharp taper. Gas outlet 905 is located in the top portion 902. During operation, gas is passed into gas inlet 904, along tube 910, through nozzle 908, out nozzle opening 909, through liquid (not depicted), through the interior 906, and out gas outlet 905. In some aspects, transporting gas through the liquid impinger causes the liquid (not depicted) to swirl within the bottom portion 903. Feature 923 depicts threads, which in this aspects allows assembly and disassembly of the liquid impinger via rotation along the threads. Feature 922 is an optional port for testing the liquid impinger.

Figure 10:
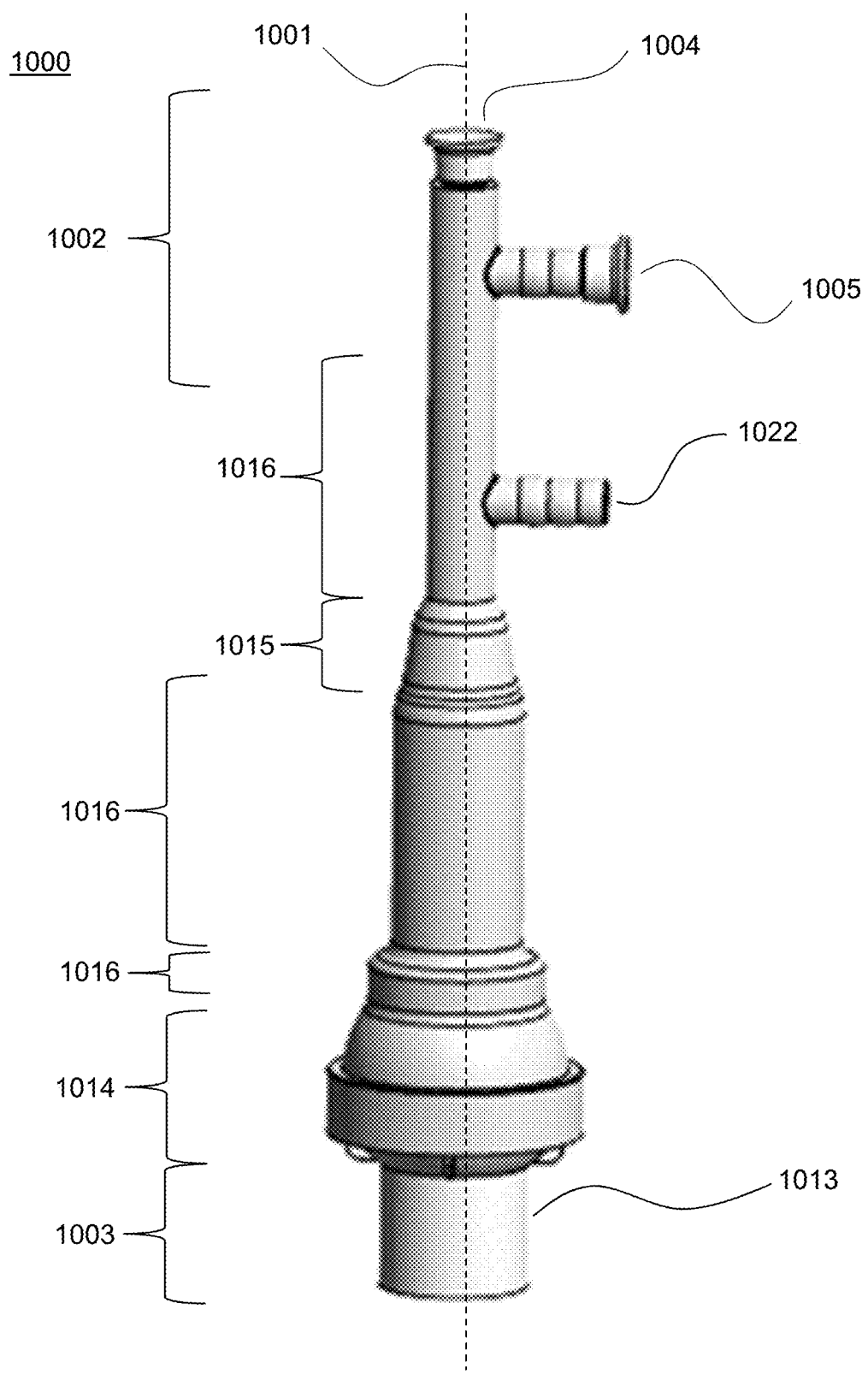
FIG. 10. depicts an exterior view of the liquid impinger of FIG. 9.

FIG. 10 depicts an exterior view of the liquid impinger of FIG. 9. Liquid impinger 1000 comprises a vertical axis 1001, a top portion 1002, a bottom portion 1003, a gas inlet 1004, a gas outlet 1005, side wall 1013, expanded portion 1014, tapered portion 1015, and three substantially straight-walled portions 1016. Feature 1022 is an optional port for testing the liquid impinger.

Figure 11:
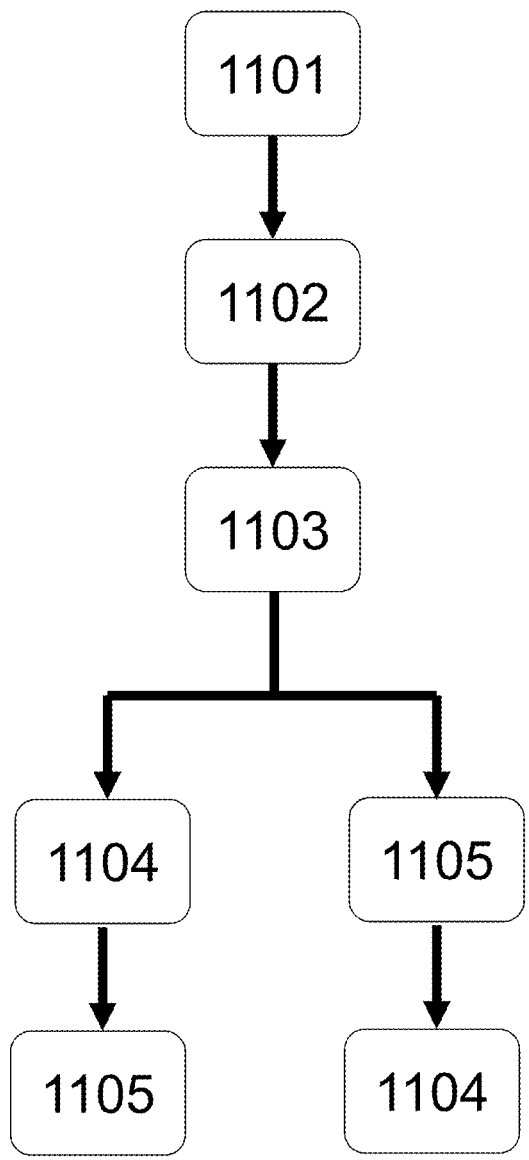
FIG. 11 depicts a flow diagram of some aspects of a method for producing a liquid impinger.
Figure 13A:
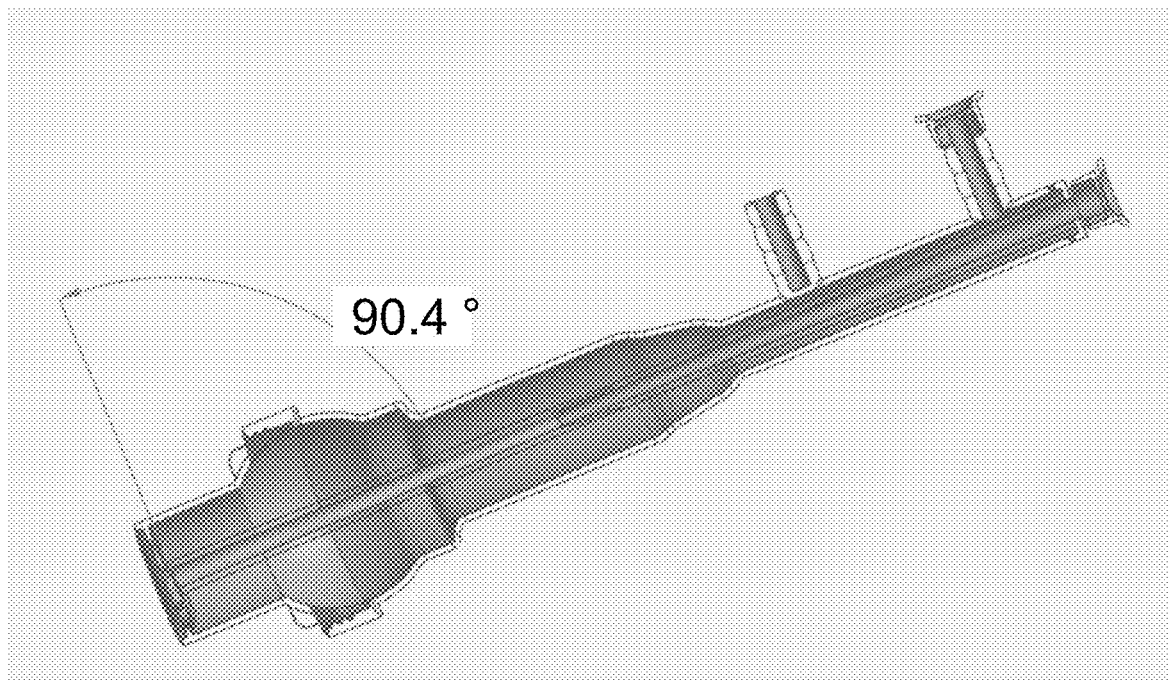
FIGS. 13A and 13B depict perspective views of a liquid impinger showing an example angular orientation of the gas inlet and tube relative to the nozzle.
Figure 13B:
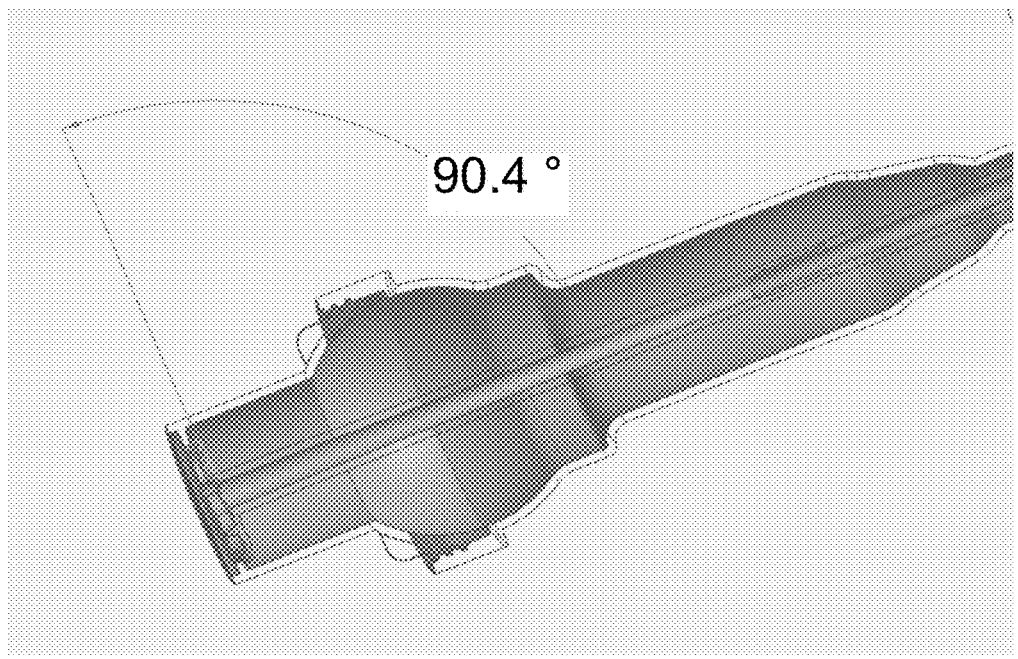
Figure 14A:
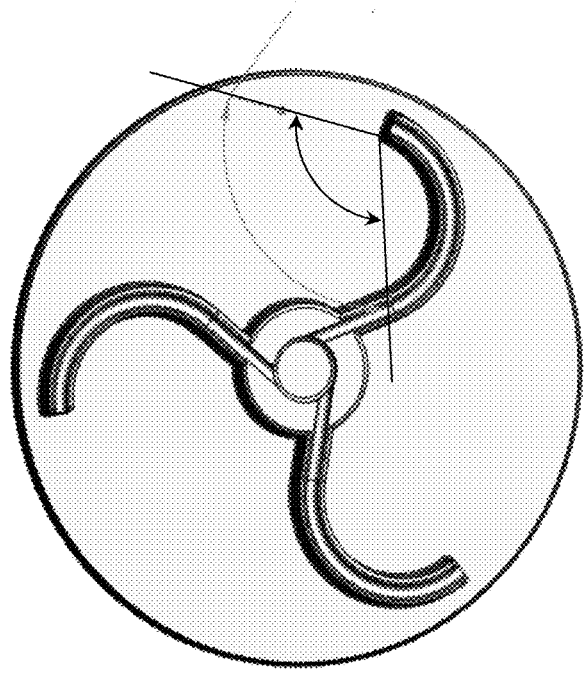
FIGS. 14A and 14B depict top views showing an example angular orientation of a nozzle of a liquid impinger.
Figure 14B:
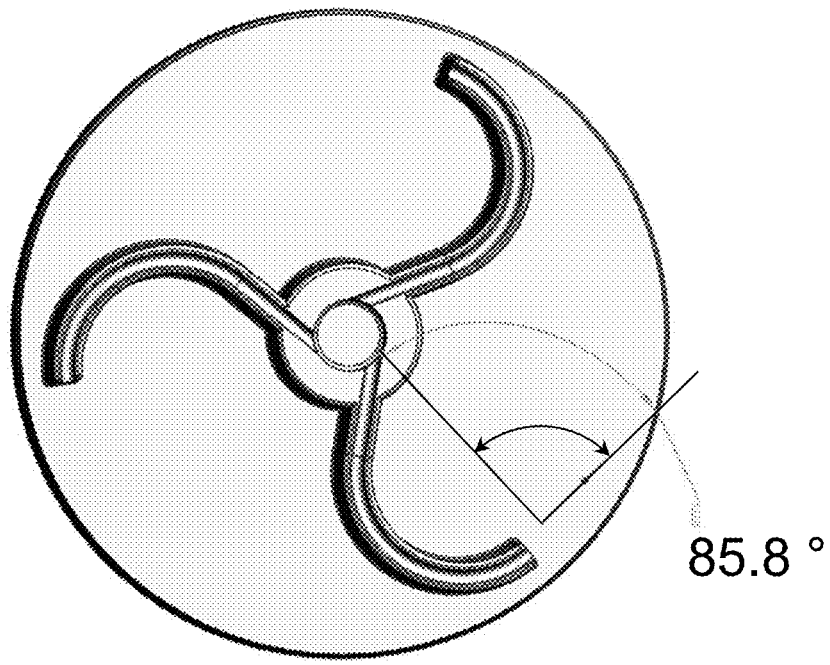

FIGS. 13A and 13B depicts perspective views of a liquid impinger of the invention showing an example angular orientation of the gas inlet and tube relative to the nozzle. FIGS. 14A and 14B depicts top views showing an example angular orientation of a nozzle of the present liquid impinger FIG. 11 depicts a flow diagram of some aspects of a method for producing a liquid impinger or a method for producing a filled and sterilized liquid impinger. Some aspects of the methods comprise a step 1101 of forming at least two components of a liquid impinger, a step 1102 of assembling the at least two components to produce an assembled liquid impinger, a step 1103 of filling a portion of the interior of the assembled liquid impinger with the liquid to produce a filled liquid impinger, and a step 1104 of exposing the filled liquid impinger to radiation to sterilize at least a portion of the liquid present in the interior of the liquid impinger, thereby producing a filled and sterilized liquid impinger. In some aspects, the method further comprises a step 1105 that is performed before or after exposing step 1104, as indicated in FIG. 11. In some aspects, any step depicted in FIG. 11 can be performed or not performed. For example, in some aspects, all steps are performed, and step 1105 takes place before or after step 1104. In some aspects, forming step 1101 is not performed and assembling step 1102 and filling step 1103 are performed. In some aspects, forming step 1101 is not performed, and assembling step 1102, filling step 1102, and exposing step 1103 are performed. In some aspects, forming step 1101 and assembling step 1102 are performed, and filling step 1103, exposing step 1104, and packaging step 1105 are not performed. In some aspects, forming step 1101, assembling step 1102, filling step 1103, and exposing step 1104 are performed. All possible combinations of steps are contemplated, and any step can be performed or not performed and combined with any other step that is performed or not performed.

FIG. 12 is described elsewhere herein to aid in understanding how the various components of the liquid impinger are attached to one another, including how the liquid impinger is assembled.

Figures 15A, 15B:
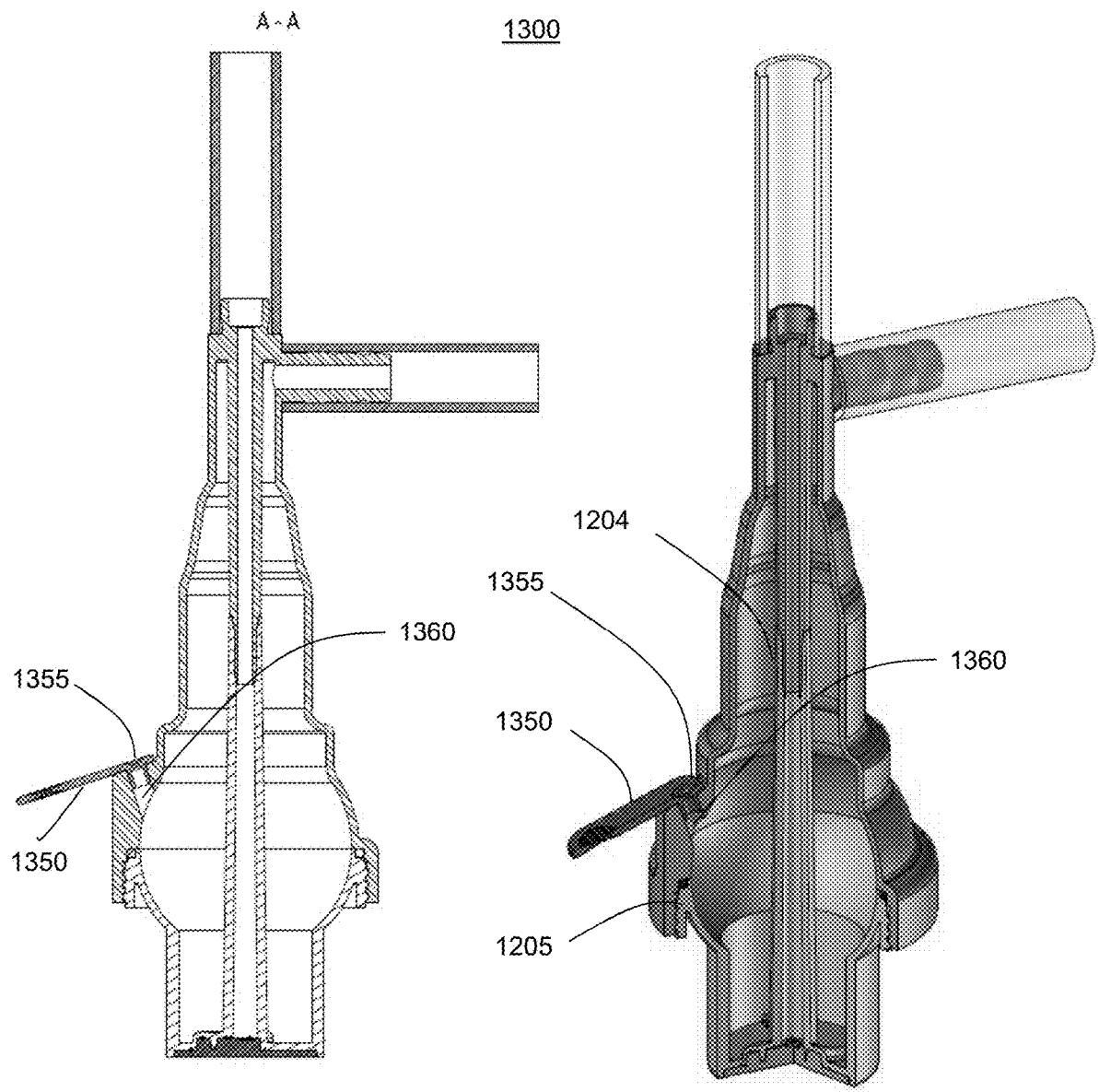
FIGS. 15A, 15B and 15C depict a cross section, a side view cut-away, and a top view of a liquid impinger.
Figure 15C:
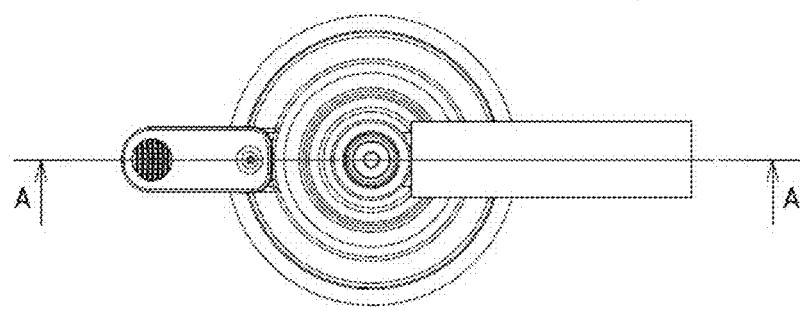

Turning now to FIGS. 15A-C, one example of liquid impinger 1300 is shown. Liquid impinger 1300 includes sample port 1360 and cap 1350. The sample port 1360 is configured to provide selective access to the liquid contained in the interior of the vessel. The cap 1350 includes a septum 1355. The septum 1355 can be made of rubber or similar material to allow a needle to penetrate the septum 1355 while maintaining the barrier between the interior of the impinger and the ambient environment.

In some embodiments, the impinger may be molded, assembled, filled with liquid media, capped, sterilized and then provided to an end user. The end user may then sample a gas stream with the liquid impinger and then extract a liquid sample by penetrating the septum with a syringe. Thus, false positives may be reduced via the sealed sampling operation facilitated by the sampling port and septum.

EXAMPLES

Aspects of the invention can be further understood by the following non-limiting examples.

Example 1: Liquid Impinger

This example demonstrates some aspects of a liquid impinger, particularly a single use, disposable liquid impinger.

A disposable impinger has the following components/characteristics: (1) ampulla in which there is liquid media, (2) a cannula of inlet to inflate air into the liquid, (3) a vacuum connection, (4) a cap for vacuum connector, (5) a cap of inlet cannula, and (6) all materials are made with plastic (e.g., a polymeric material).

Steps for producing and using the liquid impinger include: (1) components are made by molding, (2) sterilization by beta irradiation, (3) filling of media in the ampulla and assembling of the device, (4) sterilization with gamma irradiation, (5) shipping to customers, (6) positioning in to the sampling point, connecting vacuum source and inlet probe, (7) sampling, giving vacuum, (8) removal of the device from the sampling point, closing inlet and vacuum connector with caps, and (9) detection of bacteria in liquid.

Benefits of the disposable liquid impinger include (1) to have bacteria in a liquid permits an easier detection with less handling, (2) to have a sterilized closed disposable device to minimize or prevent false positive, and (3) its special design minimizes loss of liquid during sampling to enlarge monitoring time and minimize its dimensions.

The liquid Impingers and methods disclosed herein solve many issues of known samplers. For example, actual common microbiological detection in a clean room environment is often performed using petri dishes. Some solutions, such as single-use agar-filled petri dishes, permit noncontact of the media up to the growing/incubation, but the step of detection/recognition is still manual with a possible contamination made by human manipulation/intervention. In addition, the time required to incubate/grow in agar petri dishes is several days, e.g., 2-3 days. In liquid media, however, incubation/growing can be faster, and there are several methods permitting use with low handling in conjunction with detection techniques, such as PCR. It is possible to provide monitoring with a liquid impinger, but known impingers are typically made of glass and thus are not consumables (i.e., disposable), as they have to be washed and sterilized prior to each repeated use. Moreover, known liquid impingers are often too big to be ideally located at the monitoring point.

Aspects of the disposable liquid impinger described in this example are depicted, for example, in FIG. 3 and FIG. 9.

Additional aspects include:

Aspect 1. A liquid impinger, comprising:
a vessel comprising a vertical axis, a top portion, an interior, and a bottom portion comprising an interior base,
a gas inlet in fluid communication with the interior via at least one nozzle positioned in the interior and attached to the bottom portion, wherein the nozzle comprises a nozzle opening, and
a gas outlet in fluid communication with the interior,
wherein the gas inlet, the at least one nozzle, the interior, and the gas outlet sequentially define a gas flow path, and
wherein the vessel is configured to contain a liquid within the interior.

Aspect 2. The liquid impinger of aspect 1, wherein the liquid impinger comprises a polymeric material.

Aspect 3: The liquid impinger of aspect 2, or any preceding aspect, wherein the polymeric material comprises poly(acrylonitrile-butadiene-styrene), polyethylene, polycarbonate, polyamide, polystyrene, transparent polystyrene (e.g., Polystyrol™), high impact polystyrene, polypropylene, polyoxymethylene, polyurethane, rubber, or any combination thereof.

Aspect 4: The liquid impinger of any preceding aspect, wherein, when the liquid impinger contains the liquid, the at least one nozzle is submerged in the liquid, and transporting a gas along the gas flow path causes the gas to pass through the liquid.

Aspect 5. The liquid impinger of any preceding aspect, further comprising the liquid.

Aspect 6. The liquid impinger of any preceding aspect, wherein the liquid impinger is produced by a process comprising molding, injection molding, blow molding, rotational molding, additive manufacturing, three-dimensional printing, subtractive manufacturing, casting, forming, vacuum forming, extrusion, or any combination thereof, and, optionally, wherein the process produces at least three separate components that are joined together to form the liquid impinger.

Aspect 7. The liquid impinger of any preceding aspect, wherein the at least one nozzle comprises at least two nozzles or at least three nozzles.

Aspect 8. The liquid impinger of any preceding aspect, wherein each nozzle opening has a diameter of 0.1 mm to 3.2 mm.

Aspect 9. The liquid impinger of any preceding aspect, wherein the at least one nozzle comprises a shape comprising an arc.

Aspect 10. The liquid impinger of aspect 9, or any preceding aspect, wherein the arc is substantially within a plane that makes an angle with the vertical axis of 85 degrees to 95 degrees.

Aspect 11. The liquid impinger of any preceding aspect, wherein the gas inlet is connected to the at least one nozzle by a tube extending from the top portion to the bottom portion within the interior.

Aspect 12. The liquid impinger of aspect 11, or any preceding aspect, wherein the tube is substantially straight along the vertical axis.

Aspect 13. The liquid impinger of aspect 11 or aspect 12, or any preceding aspect, wherein the gas flow path bends at an angle of 80 degrees to 100 degrees between the tube and the at least one nozzle.

Aspect 14. The liquid impinger of any preceding aspect, wherein the at least one nozzle has a horizontal angle of 0 degrees to 40 degrees.

Aspect 15. The liquid impinger of any preceding aspect, wherein the at least one nozzle has a vertical angle of −40 degrees to 40 degrees Aspect 16. The liquid impinger of any preceding aspect, wherein the bottom portion comprises a cylindrical wall extending substantially along at least a portion of the vertical axis.

Aspect 17. The liquid impinger of any preceding aspect, further comprising at least one expanded portion between the bottom portion and the top portion, wherein the expanded portion has a larger internal cross-sectional area at its widest point than an internal cross-sectional area of the bottom portion at its widest point.

Aspect 18. The liquid impinger of aspect 17, or any preceding aspect, wherein the expanded portion is a substantially spherical or ellipsoidal shape.

Aspect 19. The liquid impinger of aspect 17 or aspect 18, or any preceding aspect, further comprising at least one tapered portion between the expanded portion and the top portion, wherein the at least one tapered portion tapers to a smaller internal cross-sectional area along the vertical axis toward the top portion.

Aspect 20. The liquid impinger of any one of aspects 17-19, or any preceding aspect, further comprising at least one substantially straight-walled portion between the expanded portion and the tapered portion.

Aspect 21. The liquid impinger of any one of aspects 1-15, or any preceding aspect, wherein the bottom portion comprises a substantially spherical or ellipsoidal shape.

Aspect 22. The liquid impinger of aspect 21, or any preceding aspect, further comprising at least one tapered portion between the bottom portion and the top portion, wherein the at least one tapered portion tapers to a smaller internal cross-sectional area along the vertical axis toward the top portion.

Aspect 23. The liquid impinger of any preceding aspect, wherein the bottom portion further comprises a side wall, and the nozzle opening is positioned within 10 mm of the side wall or substantially flush with the side wall.

Aspect 24. The liquid impinger of any preceding aspect, wherein the liquid impinger is configured to operate with a volume of the liquid of 15 mL to 200 mL.

Aspect 25. The liquid impinger of any preceding aspect, wherein at least a portion of the liquid impinger is composed of a material sufficiently transparent to radiation to enable sterilization of the liquid, if present, and the interior via irradiation.

Aspect 26. The liquid impinger of any preceding aspect, wherein the bottom portion is configured to be attached to or removed from the liquid impinger by rotating the bottom portion of the liquid impinger along threads in a screwing fashion.

Aspect 27. The liquid impinger of any preceding aspect, configured to be used once for monitoring a gas flow and then discarded.

Aspect 28. The liquid impinger of any preceding aspect, wherein the liquid comprises an anti-foaming agent, optionally wherein the anti-foaming agent is present in the liquid at a concentration of 0.001 vol. % to 1 vol. %.

Aspect 29. The liquid impinger of any preceding claim, wherein the vessel comprises:
a sampling port, the sampling port configured to provide selective access to the liquid in the interior of the vessel for sampling the liquid in the vessel.

Aspect 30. The liquid impinger of aspect 29, wherein the vessel comprises a removable cap for sealing the sampling port.

Aspect 31. The liquid impinger of aspect 30, wherein the cap comprises a septum, the septum being configured to receive a needle to allow a liquid to be withdrawn from the interior of the vessel while maintaining the interior of the vessel in a sealed state.

Aspect 32. A method comprising:
providing a liquid impinger of any preceding aspect or providing a liquid impinger comprising:
  a vessel comprising a vertical axis, a top portion, an interior containing a liquid, and a bottom portion comprising an interior base,
  a gas inlet in fluid communication with the interior via at least one nozzle positioned in the interior and attached to the bottom portion, wherein the nozzle comprises a nozzle opening and the nozzle opening is submerged in the liquid, and
  a gas outlet in fluid communication with the interior, and
  wherein the gas inlet, the at least one nozzle, the interior, and the gas outlet sequentially define a gas flow path
transporting a gas comprising analytes along the gas flow path and through the liquid, and
depositing in the liquid at least a portion of the analytes.

Aspect 33. The method of aspect 32, or any preceding aspect, wherein the analytes are particles, molecular analytes or a combination thereof.

Aspect 34. The method of aspect 32 or aspect 33, or any preceding aspect, wherein the liquid impinger comprises at least two components, and the method further comprises, prior to the providing step, filling the vessel with the liquid prior to or after assembly of the at least two components.

Aspect 35. The method of any one of aspects 32-34, or any preceding aspect, further comprising, prior to the transporting step, irradiating the liquid impinger in assembled form and/or filled form with radiation to sterilize at least a portion of the interior and at least a portion of the liquid contained therein, wherein at least a portion of the liquid impinger is composed of a material sufficiently transparent to the radiation to enable the sterilization.

Aspect 36. The method of any one of aspects 32-35, or any preceding aspect, wherein at least a portion of the analytes comprises biological particles.

Aspect 37. The method of any one of aspects 32-36, or any preceding aspect, further comprising, after the depositing step, incubating the liquid under conditions sufficient to facilitate growth of biological particles, wherein the liquid comprises a growth medium.

Aspect 38. The method of aspect 37, or any preceding aspect, further comprising detecting whether the biological particles are present in the liquid.

Aspect 39. The method of aspect 38, or any preceding aspect, wherein the detecting step comprises at least one of: (1) optical detection comprising at least one of visual inspection by eye, an optical detector, an imaging device, use of ultraviolet-visible, near infrared, infrared, or fluorescence spectroscopy; (2) perceiving a change in oxygen level or carbon dioxide level in the liquid; or (3) analysis of the liquid after extraction from the liquid impinger using an analytical laboratory technique optionally comprising the polymerase chain reaction (PCR), nucleotide sequencing, hybridization, restriction fragment length polymorphism (RFLP) analysis, flow cytometry, fluorescent in-situ hybridization (FISH), immunological identification, fatty acid profiling, metabolic profiling, or any combination thereof.

Aspect 40. The method of any one of aspects 36-39, or any preceding aspect, wherein at least one of the incubating step or the detecting step is performed without removing the liquid from the vessel or disassembling the liquid impinger.

Aspect 41. The method of any one of aspects 34-37, or any preceding aspect, wherein performance of the filling step and the sterilizing step in combination minimizes human contact with the liquid and reduces false positives in the detecting step.

Aspect 42. The method of any one of aspects 34-38, or any preceding aspect, further comprising, after performing one cycle of the providing, transporting, depositing, incubating, and detecting steps, at least one of: (1) discarding the liquid impinger, (2) never again sterilizing the liquid impinger in preparation for a second cycle of the providing, transporting, depositing, incubating, and detecting steps, or (3) never again performing a second cycle of the providing, transporting, depositing, incubating, and detecting steps.

Aspect 43. The method of any one of aspects 32-42, or any preceding aspect, wherein the at least one nozzle comprises at least two nozzles or at least three nozzles.

Aspect 44. The method of any one of aspects 32-43, or any preceding aspects, wherein each nozzle opening has a diameter of 0.1 mm to 3.2 mm.

Aspect 45. The method of any one of aspects 32-44, or any preceding aspect, wherein the at least one nozzle comprises a shape comprising an arc, and the arc is substantially within a plane that makes an angle with the vertical axis of 85 degrees to 95 degrees.

Aspect 46. The method of any one of aspects 32-45, or any preceding aspect, wherein the at least one nozzle has a horizontal angle of 0 degrees to 40 degrees.

Aspect 47. The method of any one of aspect 32-46, or any preceding aspect, wherein the gas inlet is connected to the at least one nozzle by a tube extending from the top portion to the bottom portion within the interior.

Aspect 48. The method of any one of aspects 32-47, or any preceding aspect, wherein the bottom portion comprises a cylindrical, spherical, or ellipsoidal shape, and the liquid impinger further comprises:

at least one expanded portion between the bottom portion and the top portion, wherein the expanded portion has a larger internal cross-sectional area at its widest point than an internal cross-sectional area of the bottom portion at its widest point, and at least one tapered portion between the expanded portion and the top portion, wherein the at least one tapered portion tapers to a smaller internal cross-sectional area along the vertical axis toward the top portion.

Aspect 49. The method of any one of aspects 32-48, or any preceding aspect, wherein the bottom portion further comprises a side wall, and the nozzle opening is positioned within 10 mm of the side wall or is substantially flush with the side wall.

Aspect 50. The method of any one of aspects 32-49, or any preceding aspect, wherein the transporting step is performed at a flow rate of 1 L/min to 20 L/min.

Aspect 51. The method of any one of aspects 32-50, or any preceding aspect, wherein the liquid impinger comprises a polymeric material.

Aspect 52. The method of aspect 51, or any preceding aspect, wherein the polymeric material comprises poly(acrylonitrile-butadiene-styrene), polyethylene, polycarbonate, polyamide, polystyrene, transparent polystyrene (e.g., Polystyrol™), high impact polystyrene, polypropylene, polyoxymethylene, polyurethane, rubber, or any combination thereof.

Aspect 53. The method of any of aspects 32-52 comprising:

in response to the transferring step, removing a sample of the liquid from the interior of the vessel via a sample port.

Aspect 54. The method of claim 53, wherein the step of removing a sample comprises inserting a needle into a septum of the sample port.

Aspect 55. A method for producing a liquid impinger, the method comprising:
forming at least two components of a liquid impinger,
optionally, assembling the at least two components to produce an assembled liquid impinger, the assembled liquid impinger comprising:
a vessel comprising a vertical axis, a top portion, an interior, and a bottom portion comprising an interior base,
a gas inlet in fluid communication with the interior via at least one nozzle positioned in the interior and attached to the bottom portion, wherein the nozzle comprises a nozzle opening, and
a gas outlet in fluid communication with the interior,
wherein the gas inlet, the at least one nozzle, the interior, and the gas outlet sequentially define a gas flow path, and
wherein the vessel is configured to contain a liquid within the interior,
optionally, filling a portion of the interior of the assembled liquid impinger with the liquid to produce a filled liquid impinger,
optionally, exposing the filled liquid impinger to radiation to sterilize at least a portion of the liquid present in the interior of the liquid impinger, thereby producing a filled and sterilized liquid impinger, and
optionally, before or after the exposing step, packaging the filled liquid impinger or the filled and sterilized liquid impinger in a manner that prevents ingress of particles or contamination into the interior of the liquid impinger.

Aspect 56. A method for producing a filled and sterilized liquid impinger, the method comprising:
a first providing step, comprising providing a filled liquid impinger, wherein the filled liquid impinger comprises:
a vessel comprising a vertical axis, a top portion, an interior, and a bottom portion comprising an interior base,
a gas inlet in fluid communication with the interior via at least one nozzle positioned in the interior and attached to the bottom portion, wherein the nozzle comprises a nozzle opening, and
a gas outlet in fluid communication with the interior,
wherein the gas inlet, the at least one nozzle, the interior, and the gas outlet sequentially define a gas flow path, and
wherein the vessel is contains a liquid within the interior,
exposing the filled liquid impinger to radiation to sterilize at least a portion of the liquid present in the interior of the liquid impinger, thereby producing the filled and sterilized liquid impinger, and
optionally, before or after the exposing step, packaging the filled liquid impinger or the filled and sterilized liquid impinger in a manner that prevents ingress of particles or contamination into the interior of the liquid impinger.

Aspect 57. The method of aspect 56, or any preceding aspect, further comprising, prior to the first providing step:
a second providing step, comprising providing an assembled liquid impinger, wherein the assembled liquid impinger comprises the filled liquid impinger without the liquid, and
filling a portion of the interior of the assembled liquid impinger with the liquid to produce the filled liquid impinger.

Aspect 58. The method of aspect 57, or any preceding aspect, further comprising, prior to the second providing step: assembling at least two components to produce the assembled liquid impinger.

Aspect 59. The method of aspect 58, or any preceding aspect, further comprising, prior to the assembling step: forming the at least two components.

Aspect 60. A method for producing a filled and sterilized liquid impinger, the method comprising:
forming at least two components of a liquid impinger,
assembling the at least two components to produce an assembled liquid impinger, the assembled liquid impinger comprising:
a vessel comprising a vertical axis, a top portion, an interior, and a bottom portion comprising an interior base,
a gas inlet in fluid communication with the interior via at least one nozzle positioned in the interior and attached to the bottom portion, wherein the nozzle comprises a nozzle opening, and
a gas outlet in fluid communication with the interior,
wherein the gas inlet, the at least one nozzle, the interior, and the gas outlet sequentially define a gas flow path, and
wherein the vessel is configured to contain a liquid within the interior,
filling a portion of the interior of the assembled liquid impinger with the liquid to produce a filled liquid impinger,
exposing the filled liquid impinger to radiation to sterilize at least a portion of the liquid present in the interior of the liquid impinger, thereby producing the filled and sterilized liquid impinger, and
optionally, before or after the exposing step, packaging the filled liquid impinger or the filled and sterilized liquid impinger in a manner that prevents ingress of particles or contamination into the interior of the liquid impinger.

Aspect 61. The method of aspect 60, or any preceding aspect, wherein the packaging step is performed and comprises (1) attaching caps to one or more gas inlets and outlets, (2) sealing the filled liquid impinger or the filled and sterilized liquid impinger into a container, or (3) a combination thereof.

Aspect 62. The method of any one of aspects 60 or 61, or any preceding aspect, wherein the forming step is performed and comprises molding, injection molding, blow molding, rotational molding, additive manufacturing, three-dimensional printing, subtractive manufacturing, casting, forming, vacuum forming, extrusion, or any combination thereof.

Aspect 63. The method of any one of aspects 60-62, or any preceding aspect, wherein the forming step is performed and forms one or more polymeric materials into the at least two components.

Aspect 64. The method of aspect 63, or any preceding aspect, wherein the one or more polymeric materials comprise poly(acrylonitrile-butadiene-styrene), polyethylene, polycarbonate, polyamide, polystyrene, transparent polystyrene (e.g., Polystyrol™), high impact polystyrene, polypropylene, polyoxymethylene, polyurethane, rubber, or any combination thereof.

Aspect 65. The method of any one of aspects 60-64, or any preceding aspect, wherein the at least two components comprises three components.

Aspect 66. The method of any one of aspects 60-65, or any preceding aspect, wherein the radiation comprises beta, gamma radiation, X-ray radiation, e-beam radiation, or any combination thereof.

Aspect 67. The method of any one of aspects 60-66, or any preceding aspect, wherein the liquid comprises a growth medium.

Aspect 68. The method of any one of aspects 60-67, or any preceding aspect, further comprising, prior to the filling step, irradiating the at least two components, the assembled liquid impinger, or both, with radiation for sterilization, the radiation comprising beta, gamma radiation, X-ray radiation, e-beam radiation, or any combination thereof.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

As used herein and in the appended claims, the singular forms "a", "an", and "the" include plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

When a Markush group or other grouping is used herein, all individual members of the group and all combinations and subcombinations possible of the group are intended to be individually included in the disclosure. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Every device, system, formulation, combination of components, or method described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method comprising:

flowing a gas through a liquid impinger, the gas comprising analytes, the liquid impinger comprising:

a vessel having a vertical axis, a top portion, an interior containing a liquid, and a bottom portion comprising an interior base;

a gas inlet in fluid communication with the interior via at least one nozzle positioned in the interior and attached to the bottom portion;

wherein the nozzle comprises a nozzle opening and the nozzle opening is submerged in the liquid; and a gas outlet in fluid communication with the interior; and wherein the gas inlet, the at least one nozzle, the interior, and the gas outlet sequentially define a gas flow path;

contacting the gas with the liquid; and in response to the contacting, transferring at least a portion of the analytes from the gas to the liquid.

2. The method of claim 1, wherein the analytes are particles, molecular analytes or a combination thereof.

3. The method of claim 1, wherein the liquid impinger comprises at least two components, and the method further comprises, prior to the providing step, filling the vessel with the liquid prior to or after assembly of the at least two components.

4. The method of claim 1, further comprising, prior to the transporting step, irradiating the liquid impinger in assembled form and/or filled form with radiation to sterilize at least a portion of the interior and at least a portion of the liquid contained therein, wherein at least a portion of the liquid impinger is composed of a material sufficiently transparent to the radiation to enable the sterilization.

5. The method of claim 1, wherein at least a portion of the analytes comprise biological particles.

6. The method of claim 1, further comprising, after the transferring step, incubating the liquid under conditions sufficient to facilitate growth of biological particles, wherein the liquid comprises a growth medium.

7. The method of claim 6, further comprising detecting whether the biological particles are present in the liquid.

8. The method of claim 7, wherein the detecting step comprises at least one of: (1) optical detection comprising at least one of visual inspection by eye, an optical detector, an imaging device, use of ultraviolet-visible, near infrared, infrared, or fluorescence spectroscopy; (2) perceiving a change in oxygen level or carbon dioxide level in the liquid; or (3) analysis of the liquid after extraction from the liquid impinger using an analytical laboratory technique optionally comprising the polymerase chain reaction (PCR), nucleotide sequencing, hybridization, restriction fragment length polymorphism (RFLP) analysis, flow cytometry, fluorescent in-situ hybridization (FISH), immunological identification, fatty acid profiling, metabolic profiling, or any combination thereof.

9. The method of claim 7, wherein at least one of the incubating step or the detecting step is performed without removing the liquid from the vessel or disassembling the liquid impinger.

10. The method of claim 1, wherein the gas inlet is connected to the at least one nozzle by a tube extending from the top portion to the bottom portion within the interior.

11. The method of claim 1 comprising:

in response to the transferring step, removing a sample of the liquid from the interior of the vessel via a sample port.

12. The method of claim 11, wherein the step of removing a sample comprises inserting a needle into a septum of the sample port.

13. The method of claim 7, further comprising, after performing one cycle of the providing, transporting, transferring, incubating, and detecting steps, at least one of: (1) discarding the liquid impinger, (2) never again sterilizing the liquid impinger in preparation for a second cycle of the providing, transporting, transferring, incubating, and detecting steps, or (3) never again performing a second cycle of the providing, transporting, transferring, incubating, and detecting steps.

14. The method of claim 1, wherein the at least one nozzle comprises at least two nozzles or at least three nozzles.

15. The method of claim 1, wherein each nozzle opening has a diameter of 0.1 mm to 3.2 mm.

16. The method of claim 1, wherein the at least one nozzle comprises a shape comprising an arc, and the arc is substantially within a plane that makes an angle with the vertical axis of 85 degrees to 95 degrees.

17. The method of claim 1, wherein the at least one nozzle has a horizontal angle of 0 degrees to 40 degrees.

18. The method claim 1, wherein the bottom portion comprises a cylindrical, spherical, or ellipsoidal shape, and the liquid impinger further comprises:

at least one expanded portion between the bottom portion and the top portion, wherein the expanded portion has a larger internal cross-sectional area at its widest point than an internal cross-sectional area of the bottom portion at its widest point, and at least one tapered portion between the expanded portion and the top portion, wherein the at least one tapered portion tapers to a smaller internal cross-sectional area along the vertical axis toward the top portion.

19. The method of claim 1, wherein the bottom portion further comprises a side wall, and the nozzle opening is positioned within 10 mm of the side wall or is substantially flush with the side wall.

20. The method of claim 1, wherein the transporting step is performed at a flow rate of 1 L/min to 20 L/min.

* * * * *